United States Patent
Deshpande et al.

(10) Patent No.: US 12,144,989 B2
(45) Date of Patent: Nov. 19, 2024

(54) SYSTEMS AND METHODS FOR RUNTIME ADAPTIVE RF POWER CONTROL FOR A COCHLEAR IMPLANT

(71) Applicant: Advanced Bionics AG, Staefa (CH)

(72) Inventors: Alok Deshpande, Thousand Oaks, CA (US); Sanat D. Ganu, Pune (IN); Yadunandan Nagarajaiah, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 428 days.

(21) Appl. No.: 17/537,718

(22) Filed: Nov. 30, 2021

(65) Prior Publication Data
US 2023/0166107 A1 Jun. 1, 2023

(51) Int. Cl.
*A61N 1/36* (2006.01)
*A61N 1/372* (2006.01)
*H04R 25/00* (2006.01)

(52) U.S. Cl.
CPC ..... *A61N 1/36038* (2017.08); *A61N 1/37223* (2013.01); *H04R 25/305* (2013.01); *H04R 25/606* (2013.01); *H04R 2225/023* (2013.01)

(58) Field of Classification Search
CPC ............ A61N 1/36038; A61N 1/37223; A61N 1/3787; H04R 25/305; H04R 25/606
See application file for complete search history.

(56) References Cited

U.S. PATENT DOCUMENTS

| | | | |
|---|---|---|---|
| 2011/0160799 A1* | 6/2011 | Mishra | H02J 50/80 607/57 |
| 2016/0220818 A1* | 8/2016 | Karunasiri | A61N 1/3787 |
| 2017/0007833 A1* | 1/2017 | Richter | A61N 1/0541 |
| 2021/0170172 A1* | 6/2021 | Irakoze | H04R 25/30 |
| 2022/0296896 A1* | 9/2022 | Griffith | A61N 1/0541 |

FOREIGN PATENT DOCUMENTS

EP 2519318 7/2011

OTHER PUBLICATIONS

Chaimanonart, et al., "Adaptive RF power control for wireless implantable bio-sensing network to monitor untethered laboratory animal real-time biological signals", Sensors, 2008 IEEE, 2008, pp. 1241-1244, doi: 10.1109/ICSENS.2008.4716668.

* cited by examiner

*Primary Examiner* — Catherine M Voorhees
(74) *Attorney, Agent, or Firm* — ALG Intellectual Property, LLC

(57) ABSTRACT

An illustrative radio frequency (RF) power control system includes an RF transmitter configured to operate external to a recipient, a cochlear implant configured to operate internal to the recipient based on RF power received from the RF transmitter, and a processor that, while operating in a power adaptation mode during which the cochlear implant applies stimulation to the recipient: 1) receives an audio signal, 2) directs the RF transmitter to provide the RF power to the cochlear implant at a power level determined based on the audio signal and based on a power level mapping function, 3) determines an error value representing a difference between a target metric and a measured metric associated with receipt of the RF power at the cochlear implant, and 4) updates the power level mapping function based on the error value. Corresponding systems and methods are also disclosed.

20 Claims, 12 Drawing Sheets

SYSTEMS AND METHODS FOR RUNTIME ADAPTIVE RF POWER CONTROL FOR A COCHLEAR IMPLANT

BACKGROUND INFORMATION

People who have little or no natural hearing may benefit from a cochlear implant system that stimulates auditory nerves in ways that natural hearing mechanisms fail to do for various reasons. For example, an electrode lead may be inserted into a cochlea of a recipient and stimulation current may be applied by electrodes on the lead as directed by a cochlear implant implanted within the recipient. One way of delivering power to the cochlear implant and the electrode lead is for a radio frequency (RF) transmitter external to the recipient to provide RF power through the recipient's skin. For example, RF power may be delivered by way of inductive coupling of an external coil associated with the RF transmitter and an internal coil associated with the cochlear implant. Internally, the RF power may then be filtered, regulated, converted from RF to direct current (DC), and/or otherwise prepared for use in powering the cochlear implant.

Since limited or no internal power storage may be available within the cochlear implant, it may be desirable for the RF transmitter to deliver the RF power at a power level that dynamically matches the power level needed by cochlear implant operations being performed under stimulation conditions as they are presently constituted (e.g., the present sound processing program, the present stimulation intensity, etc.). For example, if the RF power is provided at too low a power level, the cochlear implant may fail to properly stimulate the recipient in accordance with the desired volume and/or other target parameters, while if the RF power is provided at too high a power level, superfluous power may be wasted, leading to inefficiency and/or other issues (e.g., sub-optimal battery life, unwanted heat, etc.).

Accordingly, one-time, dedicated power calibration procedures have conventionally been used at system startup to address these competing goals of power efficiency and power sufficiency. Based on such calibration, cochlear implant systems may ensure that sufficient yet efficient RF power levels are provided during system operation.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
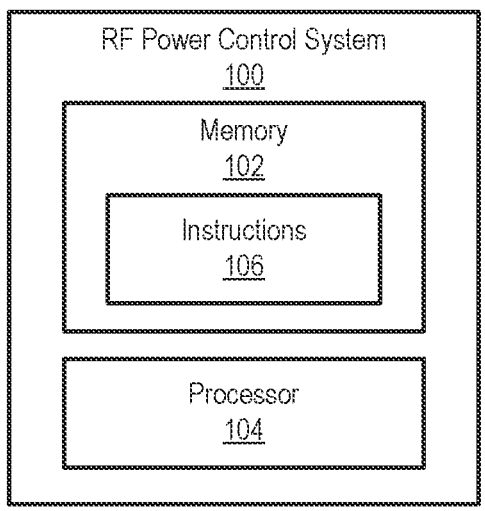
FIG. 1 shows an illustrative implementation of a radio frequency (RF) power control system for runtime adaptive RF power control for a cochlear implant.

Systems and methods for runtime adaptive radio frequency (RF) power control for a cochlear implant are described herein. On startup (or at another suitable time), conventional cochlear implant systems may go into a calibration mode during which a number of calibration tests are performed to define a power use model that will be used during normal operation to allow power to be provided at a power level that balances function and efficiency. Such a calibration mode serves to address the fact that a power level provided by an external RF power transmitter is transformed (e.g., reduced, attenuated, etc.) by an amount that is unknown and difficult to accurately predict before being received and used by an internal cochlear implant. For example, the transfer function of external RF power to become internal DC power ready for use by the cochlear implant may be affected by varied factors outside the control of the system, including: the proximity and alignment of a headpiece housing an RF coil that transmits RF power, the length of a cable coupling the headpiece with a sound processor housing the battery and RF transmitter circuitry, the amount of power needed for proper implant operation given a particular set of circumstances, the thickness of the skin between the headpiece and the cochlear implant, and a variety of other factors.

During a dedicated calibration procedure in a calibration mode, RF power at different power levels (e.g., corresponding to different types of sounds, different environments, different sound processing programs, different volumes, etc.) may be provided by the external RF power transmitter to the cochlear implant once the cochlear implant system is setup (e.g., once the headpiece is in place over the cochlear implant, etc.) and powering on. At each of these different power levels, a calibration management system may detect and store the supply voltage (or another such parameter) of the power that is ultimately delivered to the cochlear implant. In this way, a power use model may be created that can be used later (e.g., during normal operation after calibration is complete) to facilitate the RF transmitter in providing RF power at a power level that simultaneously provides sufficient energy for proper functionality of the cochlear implant while also being efficient so as to avoid needlessly draining the battery power of the system and/or creating other inefficiency issues for the system.

There are many benefits to an efficient and well-calibrated system. For example, high efficiency may allow for longer battery life and/or reduced system size and weight (due to smaller batteries lasting longer). Given that a cochlear implant system is a portable, battery-powered system that must be carried and worn any time a recipient wishes to engage with the world in ways that involve sound, even small improvements in these areas may amount to highly-desirable benefits for the system. Unfortunately, however, conventional calibration processes that result in these and other benefits tend to have various shortcomings and limitations.

For example, the time that a cochlear implant system spends in a calibration mode (typically at startup time) is time that the system is not in a stimulation mode or normal mode of operation during which the recipient is actually conveyed a sense of hearing. Accordingly, a dedicated calibration process may add several seconds to the time recipients must wait every time they put on their cochlear implant systems and power them up before they can begin hearing. This delay is compounded as well because of how sensitive the calibration process may be to small changes in how the system is worn (e.g., precisely how the headpiece is aligned on the head, etc.). Because recipients tend to make adjustments to these important parameters as they put on their systems (e.g., adjusting the headpiece to be comfortable, moving hair out of the way, etc.), and because the calibration must account for not only recipients who tend to quickly finish with such adjustments but also those who take their time, a one-shot calibration process must not even be started until it can be confidently determined that the adjustments are complete.

Even if power calibration on startup is performed perfectly (avoiding problems in which the calibration is performed while the headpiece is still in transit to its final place on the head), additional issues along these lines may still occur when later adjustments are inevitably made (e.g., due to user movements, later adjustments to the headpiece, etc.). For example, if the headpiece is bumped or adjusted slightly, the power transfer function from the RF transmitter to the cochlear implant may change such that the power use model created based on the startup calibration may become inaccurate and the system may end up providing more power to the implant than what is necessary or insufficient power that could affect sound perception (e.g., due to insufficient compliance voltage) or even cause stimulation cutouts. However, even though recalibration would be helpful in this type of situation, the constraints of conventional calibration processes may make startup time the only practical time that such calibration may be performed. For example, it may not be desirable for a recalibration to take place any time after the initial system startup since stimulation mode would need to be exited for several seconds or longer (during which the recipient may not be able to hear) as the system reenters calibration mode.

Also related to time constraints of a dedicated, formal calibration process are limits placed on how detailed the calibration can be. While the most optimal results may be achieved by carefully measuring and remeasuring many points incorporated within a power use model being generated, it may not be practical to achieve this degree of precision due to the time it would take. To keep calibration to a few seconds and not inconvenience the recipient too much during startup, various non-linearities and other nuances of RF power modeling may be overlooked for the simple reason that it would take too much time to fully account for these details.

As another example limitation of a dedicated calibration procedure, performing calibration mode tests to model the power level mapping function requires not only that natural sounds (e.g., environmental or ambient sounds in the recipient's environment, other input sound the recipient desires to hear, etc.) not be presented to the recipient, but also that test stimulation is transmitted to the cochlear implant. For example, the test stimulation may comprise various tones and/or other calibration-specific audio content used to properly model the power transfer function at various frequencies and under various conditions. In some cases, the power delivered with this test stimulation may be disposed of in a quiet and nonintrusive way, but in other cases (e.g., for certain systems, for certain recipients, given certain circumstances, etc.), the calibration test stimulation may actually be heard or otherwise perceived by the recipient. This may be annoying and inconvenient to the recipient as the cochlear implant system is coming online, but minimizing charge leakage to patient tissue during calibration mode may be difficult to accomplish entirely by way of the cochlear implant's hardware features (e.g., DAC isolation, ground switches, etc.), which may be used to internally shunt the static stimulation load. If such features are not available, the calibration testing being performed may be even more limited and constrained to minimized current leakage to the recipient's tissue.

To address these and other shortcomings and limitations of conventional calibration-based approaches, systems and methods described herein relate to runtime adaptive RF power control for a cochlear implant. As will be described in more detail below, such RF power control may be adapted in real time (e.g., at runtime during normal operation of the cochlear implant system) so as to be self-correcting, self-learning, and, in certain implementations, completely calibration-less (as will be described in more detail below, a mixed mode that leverages a full-fledged or abbreviated calibration process may also be implemented to provide various advantages). More specifically, as will be described in detail below, approaches to RF power control described herein provide all the benefits of calibrated systems while mitigating or eliminating many or all of the disadvantages and limitations that have been described for dedicated calibration procedures. For example, systems and methods described herein may gradually determine, then continuously update and optimize, a power use model referred to herein as a power level mapping function. Such power level mapping functions may be used for RF power control and may be derived and updated based on audio content that is conveyed to the recipient (e.g., ambient sound or other natural sound that is presented to the recipient) rather than (or, in certain mixed mode implementations, in addition to) being derived based on special test stimulation provided during a calibration mode such as described above.

In this way, the delays associated with dedicated startup calibration procedures may be reduced or avoided entirely (leading to significantly faster and more convenient system startup), physical adjustments to the headpiece after startup may be accounted for on the fly and in real time without having to enter (or reenter) a dedicated calibration mode, and a progressively detailed and accurate power level mapping function may be learned and fine-tuned over time without inconveniencing the recipient in any way (e.g., such as by disallowing the recipient from hearing as calibration procedures are carried out). Moreover, because the dynamic power level mapping function developed and refined in this way is based on actual audio content that is to be conveyed to the recipient (rather than artificial tones or other test stimulation that is to be shunted and not presented to the recipient), the learned model represented by the evolving power level mapping function may more closely match a true, ground-truth power use model over the dynamic range of stimulation loads specific to the particular recipient and/or his or her particular circumstances (e.g., sound processing program, sound conditions, skin flap thickness, other patient specific system parameters, etc.).

Accordingly, all of the benefits of calibration may be provided by systems and methods described herein without the drawbacks of conventional calibration-based approaches. Ultimately, sufficient yet efficient power levels may be continuously provided by an RF transmitter to a cochlear implant to provide reduced or eliminated delay at startup before stimulation begins, optimized battery usage for extended battery runtime and/or reduced battery size, use of more comfortable magnets (since the need is mitigated to hold the headpiece so rigidly in place as to avoid recalibration), quality of operation as stimulation circuits operate at specified supply voltage rails at all times, prevention of loss of lock with the cochlear implant, and various other benefits described herein.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Systems and methods described herein for runtime adaptive RF power control for a cochlear implant may provide any of the benefits mentioned above, as well as various additional and/or alternative benefits that will be described and/or made apparent below.

FIG. 1 shows an illustrative RF power control system 100 ("system 100") configured to manage RF power control for a cochlear implant in a manner that is runtime adaptive and that may or may not utilize any dedicated calibration procedure. System 100 may be implemented in different ways and/or by different components of a cochlear implant system or device associated with a cochlear implant system (e.g., a mobile device communicatively coupled to the cochlear implant system, a clinician fitting device, etc.). While certain examples described herein may focus on particular implementations of RF power control systems, it will be understood that it may be possible for other types of implementations to employ the principles being described (e.g., taking the place of the specific RF power control system implementations being described or operating in concert with those specific implementations).

System 100 may be implemented by computing resources such as an embedded computing system of a cochlear implant system. For example, computing resources embedded in a sound processor, a cochlear implant, a device coupled to the cochlear implant system (e.g., a mobile device such as a smartphone or music player, etc.), and/or another suitable device or system component may serve to perform the operations of system 100 as these operations are described herein. As will be described and illustrated in more detail below, certain implementations of system 100 may include only the computing resources (e.g., processors, memory, etc.) configured to perform operations described herein, while other implementations may further incorporate various other components of the cochlear implant system that relate to the RF power control (e.g., RF transmitters, cochlear implants, etc.). As example of one such implementation will be described and illustrated below in relation to FIG. 2.

As illustrated in FIG. 1, this example implementation of system 100 includes, without limitation, a memory 102 and a processor 104 selectively and communicatively coupled to one another. Memory 102 and processor 104 may each include or be implemented by computer hardware that is configured to store and/or execute computer instructions (e.g., software, firmware, etc.). Various other components of computer hardware and/or software not explicitly shown in FIG. 1 may also be included within an implementation of system 100. In some examples, memory 102 and processor 104 may be distributed between multiple devices as may serve a particular implementation.

Memory 102 may store and/or otherwise maintain executable data used by processor 104 to perform any of the functionality described herein. For example, memory 102 may store instructions 106 that may be executed by processor 104. Memory 102 may be implemented by one or more memory or storage devices, including any memory or storage devices described herein, that are configured to store data in a transitory or non-transitory manner. Instructions 106 may be executed by processor 104 to cause system 100 to perform any of the functionality described herein. Instructions 106 may be implemented by any suitable application, software, firmware, script, code, and/or other executable data instance. Additionally, memory 102 may also maintain any other data accessed, managed, used, and/or transmitted by processor 104 in a particular implementation.

Processor 104 may be implemented by one or more computer processing devices, including general purpose processors (e.g., central processing units (CPUs), microprocessors, etc.), special purpose processors (e.g., application-specific integrated circuits (ASICs), field-programmable gate arrays (FPGAs), etc.), or the like. Using processor 104 (e.g., when processor 104 is directed to perform operations represented by instructions 106 stored in memory 102), system 100 may perform functions associated with runtime adaptive RF power control for a cochlear implant system as described herein and/or as may serve a particular implementation.

Figure 2:
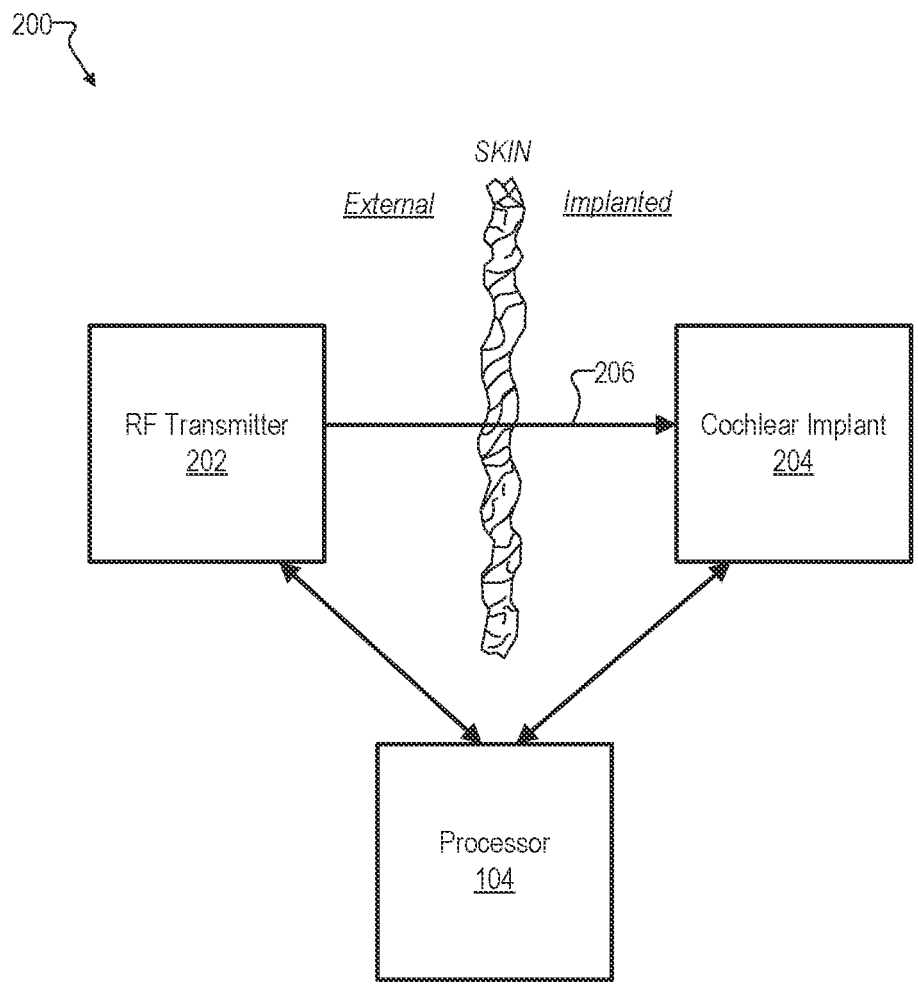
FIG. 2 shows another illustrative implementation of an RF power control system for runtime adaptive RF power control for a cochlear implant.

FIG. 2 shows another illustrative implementation of an RF power control system for RF power control without calibration. Specifically, like system 100, an RF power control system 200 ("system 200") illustrated in FIG. 2 is shown to include an implementation of processor 104 that will be understood to perform functions as directed by instructions stored in a suitable memory or storage facility (e.g., memory 102 or something similar), which is not explicitly shown in FIG. 2. However, in contrast to system 100, system 200 is shown to explicitly include an RF transmitter 202 that may be configured to operate external to a recipient (i.e., outside of the recipient's skin, as shown) and a cochlear implant 204 that may be configured to operate internal to the recipient (i.e., implanted under the recipient's skin, as shown). RF transmitter 202 may provide RF power 206 to cochlear implant 204 and cochlear implant 204 may operate based on (e.g., using) RF power 206 received from RF transmitter 202.

As shown, processor 104 may be communicatively coupled to both RF transmitter 202 and to cochlear implant 204 as processor 104 executes instructions to control the delivery of RF power 206 from RF transmitter 202 to cochlear implant 204. As will be described in more detail below, processor 104 may be implemented in any of various external or internal devices or components of the cochlear implant system that includes RF transmitter 202 and cochlear implant 204. Additionally, in certain examples, processor 104 may represent a plurality of processors implemented in different devices (e.g., internal and external devices, etc.) that collectively perform RF power control functionality described herein.

Figure 3:
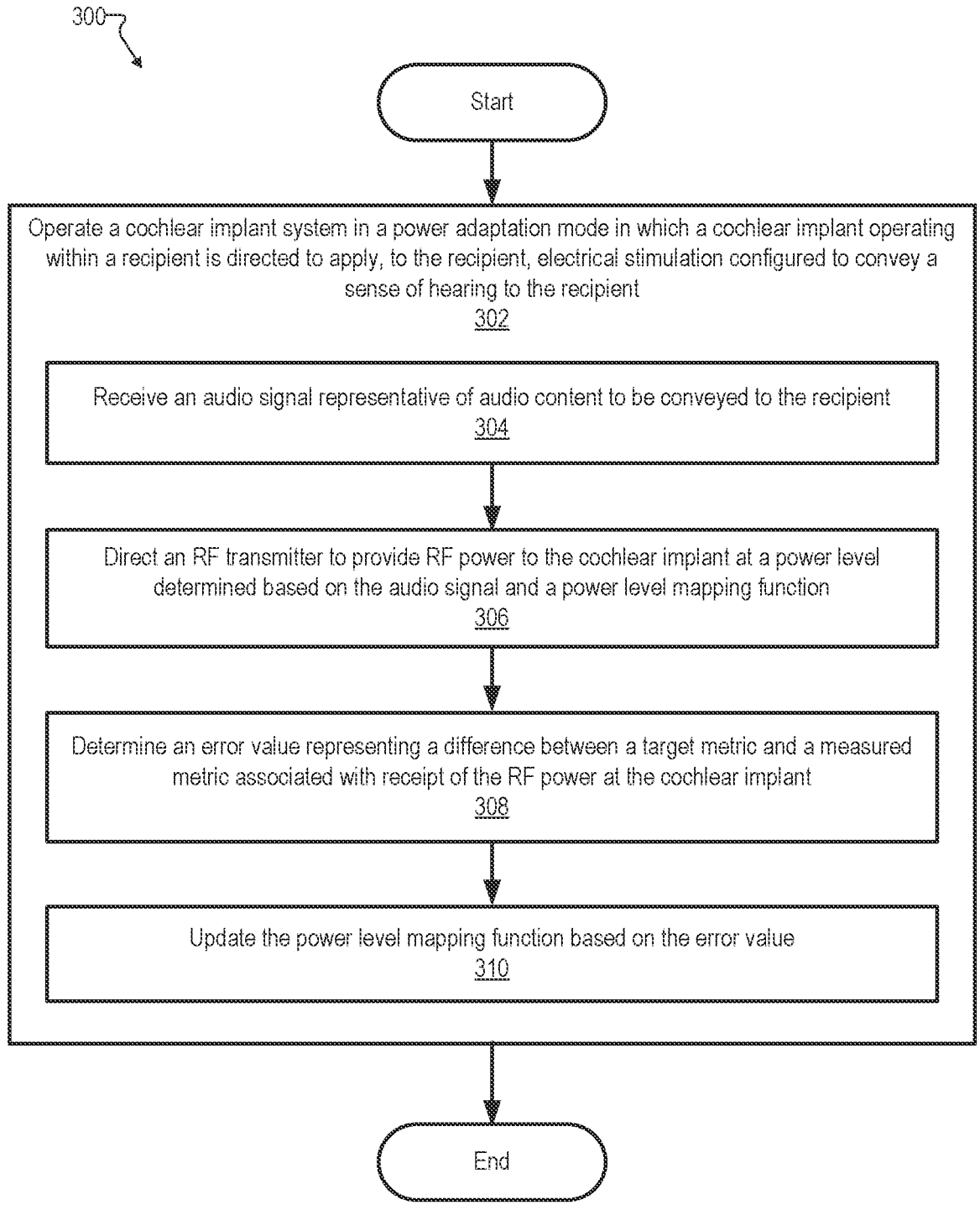
FIG. 3 shows an illustrative method for runtime adaptive RF power control for a cochlear implant.

As one example of functionality that processor 104 may perform, FIG. 3 shows an illustrative method 300 for runtime adaptive RF power control for a cochlear implant. While FIG. 3 shows illustrative operations according to one embodiment, other embodiments may omit, add to, reorder, and/or modify any of the operations shown in FIG. 3. In some examples, multiple operations shown in FIG. 3 or described in relation to FIG. 3 may be performed concurrently (e.g., in parallel) with one another, rather than being performed sequentially as illustrated and/or described. One or more of the operations shown in FIG. 3 may be performed by an RF power control system such as system 100, system 200, and/or any implementation thereof. For instance, method 300 may be performed by an RF power control system implemented within a sound processor of a cochlear implant system, or within another suitable system or device as may serve a particular implementation.

In some examples, the operations of FIG. 3 may be performed in real time so as to provide, receive, process, and/or use data described herein immediately as the data is generated, updated, changed, exchanged, or otherwise becomes available. Moreover, certain operations described herein may involve real-time data, real-time representations, real-time conditions, and/or other real-time circumstances. As used herein, "real time" will be understood to relate to data processing and/or other actions that are performed immediately, as well as conditions and/or circumstances that are accounted for as they exist in the moment when the processing or other actions are performed. For example, a real-time operation may refer to an operation that is performed immediately and without undue delay, even if it is not possible for there to be absolutely zero delay. Similarly, real-time data, real-time representations, real-time conditions, and so forth, will be understood to refer to data, representations, and conditions that relate to a present moment in time or a moment in time when decisions are being made and operations are being performed (e.g., even if after a short delay), such that the data, representations, conditions, and so forth are temporally relevant to the decisions being made and/or the operations being performed.

Each of operations 302-310 of method 300 will now be described in more detail as the operations may be performed by an RF power control system such as system 100 (which may be communicatively coupled to an RF transmitter operating external to a recipient and a cochlear implant operating internal to the recipient), system 200 (which may include such an RF transmitter and cochlear implant), or another suitable implementation.

At operation 302, the RF power control system may operate in a power adaptation mode. As shown, operation 302 is shown to incorporate the remainder of the operations of method 300 (i.e., operations 304-310), rather than being performed separately or sequentially with the other operations. Accordingly, it will be understood that each of operations 304-310 may be performed while processor 104 (and the cochlear implant system generally) operates in the power adaptation mode.

The power adaptation mode may be any suitable mode of operation in which a power level mapping function is adapted (e.g., by way of self-learning and other adaptive runtime operations) other than modes requiring dedicated calibration operations such as have been described (e.g., dedicated calibration modes involving special calibration stimulation such as artificial tones or the like, special calibration tests, etc.). For example, the power adaptation mode may be an operating mode (also referred to a normal operating mode or a stimulation mode) during which the cochlear implant system directs the cochlear implant to apply, to the recipient, electrical stimulation configured to convey a sense of hearing to the recipient. In the normal operating mode, the stimulation applied to the recipient is representative of natural sounds (e.g., environmental sounds captured by a microphone, prerecorded sounds such as music, etc.) that the recipient wishes to hear, rather than synthesized sounds (e.g., tones or other calibration stimulation) that are developed specifically for use in calibration and/or other such system management processes (and are not necessarily intended for presentation to the recipient).

While operations 304-310 are shown in FIG. 3 and described below as being performed in the power adaptation mode of operation 302 (which may be understood to be distinct from a dedicated calibration mode), it will be understood that, in certain implementations, the RF power control system may also operate in a dedicated calibration mode (e.g., prior to operating in the power adaptation mode at operation 302, not explicitly shown in method 300). For example, as will be described in more detail below, while certain implementations may operate entirely without a dedicated calibration procedure, other implementations (e.g., "mixed" implementations) may utilized a dedicated calibration procedure (e.g., a full-fledged procedure or a relatively rudimentary or abbreviated procedure that can be performed quickly and efficiently) to obtain a reasonable initialization or starting point for the run-time adaptive RF power control.

At operation 304, the RF power control system may receive an audio signal representative of audio content to be conveyed to the recipient. For example, the audio signal may represent audio content such as environmental sound captured by a microphone that the recipient wears, broadcast sound captured by a remote microphone worn by another person other than the recipient (e.g., a microphone used by a person giving a speech that the recipient is attending, etc.), prerecorded sound (e.g., music, a podcast, an audiobook, etc.) that the user has selected to be played back by the cochlear implant system (e.g., by connecting an audio player device via an audio cable or a wireless protocol such as Bluetooth), or any other natural sound that is to be presented to the recipient in the power adaptation mode.

At operation 306, the RF power control system may direct the RF transmitter to provide RF power to the cochlear implant at a power level determined based on the audio signal and based on a power level mapping function. For example, various processed system variables associated with the audio signal may be used in connection with the power level mapping function (e.g., used as inputs to the power level mapping function as described in more detail below) to determine an advantageous power level that the RF transmitter is to provide at a particular time. Such processed system variables may be representative of an overall load of the recipient's actual electrical stimulation and may include, for example, an averaged stimulation current over a certain time window, a characteristic of the audio signal itself (e.g., the volume or sound intensity of the audio signal, etc.), or the like. The power level of the transmitted RF power may be determined based on the audio signal and the power level mapping function at operation 306 by any such processed system variables associated with the audio signal being used as inputs to the power level mapping function to determine (as an output of the power level mapping function) the power level that is to be provided for the RF power.

Along with processed system variable directly related to the stimulation load of the cochlear implant, it will also be understood that other dynamic implant loads may be accounted for in determining the power level to be delivered by the transmitted RF power. For example, variables representative of other implant loads may relate to whether back-telemetry is operational or disabled, whether a recording amplifier is operational or disabled (and which operating mode the amplifier is in), whether an implantable battery is present in the system and is charging in a particular mode (e.g., pre-charging, CC phase, CV phase, etc.), or the like. These variables may be extracted from outgoing forward telemetry traffic (e.g., based on the audio signal or processed system variables associated therewith) and/or through suitable controls from the processor running RF power management. These variables may then be accounted for in the implant load estimate (e.g., as an equivalent "phantom" stimulation load, etc.). In still other examples, other static implant loads may be present that would be different across patients and/or sound processing programs. Due to the static nature of such loads during a particular session, these may be accounted for by a static offset parameter.

As has been mentioned, any of these variables may be used in connection with a dynamic power level mapping function to determine the power level that is to be used in transmitting the RF power. As will be described in more detail below, the power level mapping function may be continuously updated and refined outside of any dedicated calibration process (e.g., within power adaptation modes such as normal operation modes) to ensure that the full power transfer function from the RF transmitter to the cochlear implant is dynamically accounted for, even if variables affecting that transfer function (e.g., how the headpiece is oriented with respect to the cochlear implant, etc.) dynamically change during the operating session.

At operation 308, the RF power control system may determine an error value representing a difference between a target metric and a measured metric associated with receipt of the RF power at the cochlear implant. This error value may be used to determine whether, and to what extent, the presently-constituted power level mapping function is accurate. In other words, as the error value is continuously computed and tracked as different inputs are fed into to the power level mapping function during a normal operating session in the power adaptation mode, the RF power control system may gather data points indicative of the accuracy of the power level mapping function for various types of real-world and real-time circumstances. The target and measured metrics associated with the receipt of the RF power at the cochlear implant may be any suitable metrics as will be described in more detail below. As a few examples, the target and measured metrics used to determine the error value may relate to a supply voltage at which the cochlear implant receives the RF power (e.g., a tank voltage, etc.) or to another suitable metric associated with verifiable RF power delivery to the cochlear implant as will be described in more detail below or as may serve a particular implementation.

At operation 310, the RF power control system may update the power level mapping function based on the error value. For example, an adaptive algorithm, an artificial intelligence (AI) or machine-learning technology, or another suitable technique may be used to make adjustments to the power level mapping function being continuously used at operation 306 with a goal of keeping the error value (being continuously computed at operation 308) as close to zero as possible. In other words, to the extent that the measured metric at the cochlear implant differs from a target metric representing an optimal (e.g., both sufficient and efficient) power level for the cochlear implant under the present conditions, the RF power control system may update the power level mapping function to try to eliminate this divergence under all of the conditions that have been observed for the cochlear implant system in the session.

Any suitable technique, approach, technology, or methodology may be used at operation 310 to update the power level mapping function based on the error value. For example, a Kalman filter, a least mean squares algorithm, a recursive least squares algorithm, a proportional-integral-derivative (PID) control loop, or another suitable type of adaptive feedback loop, feedback/feedforward control technique, or other control algorithm may be employed to update the power level mapping function in a manner aimed to keeps the error value near to zero. As another example, an AI technology (e.g., a convolutional neural network, a DNN structure, etc.) may be utilized to gradually learn the power level mapping function during normal operation of the system. For example, a training phase for the AI technology may involve multiple system parameters (e.g., triads of average stimulation current, RF level, and tank voltage) and the final power level mapping function (e.g., the true underlying model) may be fed to the AI module. The trained AI network may reside in the system and may use the runtime-measured parameters to continually predict the power level mapping function for the present scenario as conditions change.

Figure 4:
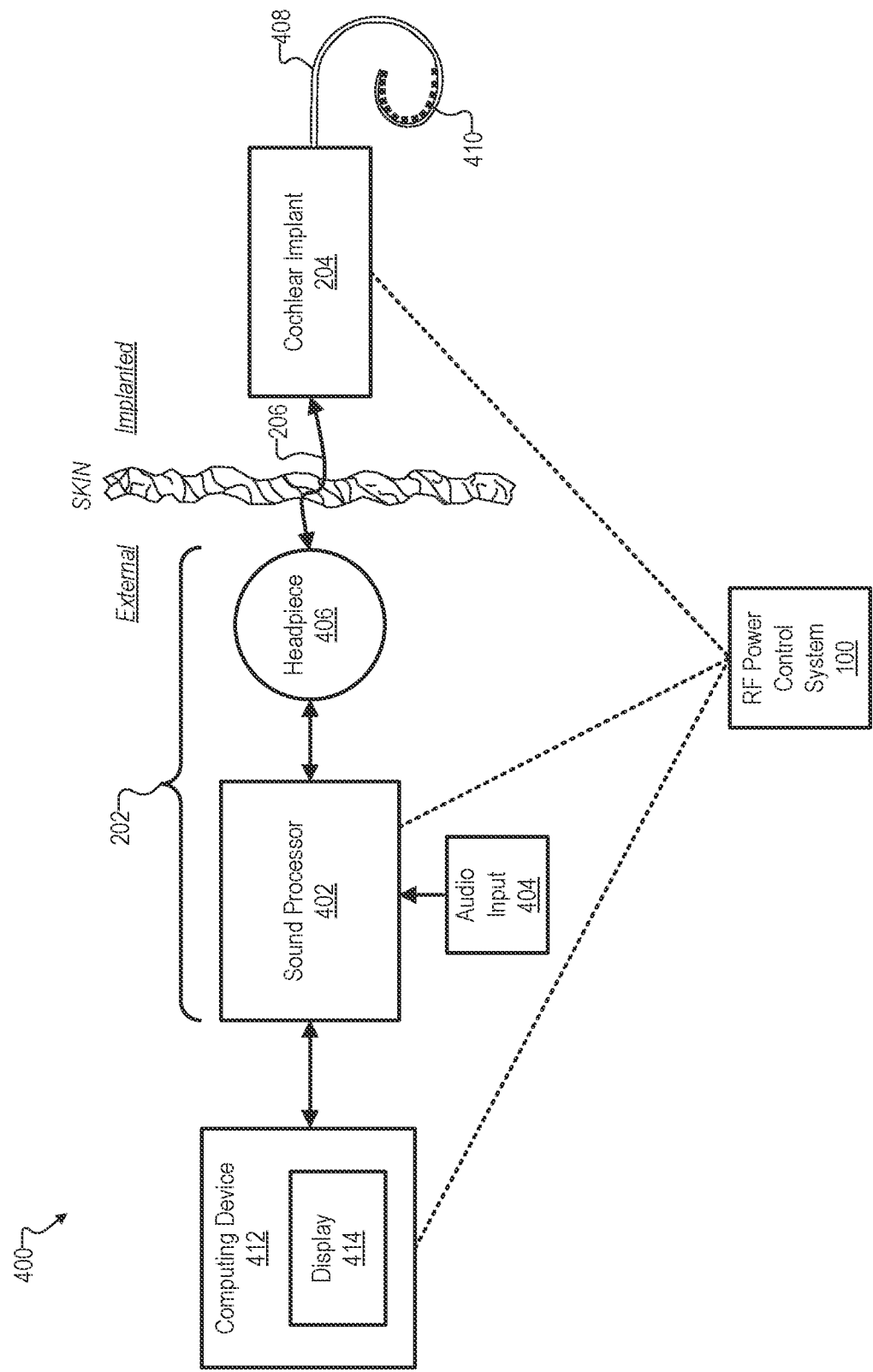
FIG. 4 shows illustrative aspects of a cochlear implant system in which an implementation of an RF power control system may operate.

FIG. 4 shows illustrative aspects of a cochlear implant system 400 in which an implementation of an RF power control system such as system 100 or system 200 may operate to perform operations such as those of method 300. While not explicitly shown in FIG. 4, it will be understood that cochlear implant system 400 may be used by a recipient within whom cochlear implant 204 may be implanted. As shown, cochlear implant system 400 may include a sound processor 402 that receives an audio input 404, a headpiece 406 that transmits RF power 206 to an implementation of cochlear implant 204, and an electrode lead 408 having a plurality of electrodes 410. In some examples, cochlear implant system 400 may include a computing device 412 having a display 414, or may at least be communicatively coupled to such a device even if the device is separate from (i.e., not included within) cochlear implant system 400.

As shown by dotted lines extending from an implementation of system 100 to various components of cochlear implant system 400 in FIG. 4, system 100 may be implemented by any of various computing devices in the setup shown in FIG. 4. For example, system 100 may be implemented by computing resources in sound processor 402, cochlear implant 204, computing device 412, and/or by any combination of these computing resources and/or those of other suitable devices not explicitly shown in FIG. 4. Similarly, an example of how the components of system 200 (i.e., RF transmitter 202, cochlear implant 204, and RF power 206) may be implemented is also shown in FIG. 4. Specifically, RF transmitter 202 may be implemented by circuitry within sound processor 402 and headpiece 406 (e.g., a battery and an RF power transmission circuit implemented in sound processor 402, an inductive coil implemented in headpiece 406, a cable connecting sound processor 402 and headpiece 406, etc.) to transmit RF power 206 through the recipient's skin to cochlear implant 204.

Cochlear implant system 400 shown in FIG. 4 is a unilateral cochlear implant system (i.e., associated with only one ear of the recipient). Alternatively, a bilateral configuration of cochlear implant system 400 may include separate cochlear implants and electrode leads for each ear of the recipient. In the bilateral configuration, sound processor 402 may be implemented by a single processing unit configured to interface with both cochlear implants or by two separate processing units each configured to interface with a different one of the cochlear implants.

Cochlear implant 204 may be implemented by any suitable type of implantable stimulator. For example, cochlear implant 204 may be implemented by an implantable cochlear stimulator. Additionally or alternatively, cochlear implant 204 may be implemented by a brainstem implant and/or any other type of device that may be implanted within the recipient and configured to apply electrical stimulation to one or more stimulation sites located along an auditory pathway of the recipient.

In some examples, cochlear implant 204 may be configured to generate electrical stimulation representative of an audio signal (e.g., from audio input 404) that is processed by sound processor 402 in accordance with one or more stimulation parameters transmitted to cochlear implant 204 by sound processor 402. Cochlear implant 204 may be further configured to apply the electrical stimulation to one or more stimulation sites (e.g., one or more intracochlear locations) within the recipient by way of one or more electrodes 410 on electrode lead 408. In some examples, cochlear implant 204 may include a plurality of independent current sources each associated with a channel defined by one or more of electrodes 410. In this manner, different stimulation current levels may be applied to multiple stimulation sites simultaneously by way of multiple electrodes 410.

Cochlear implant 204 may additionally or alternatively be configured to generate, store, and/or transmit data. For example, cochlear implant may use one or more electrodes 410 to record one or more signals (e.g., one or more voltages, impedances, evoked responses within the recipient, and/or other measurements) and transmit, by way of a communication link (e.g., a same inductive link over which RF power 206 is transmitted through the skin), data representative of the one or more signals to sound processor 402. This data may be referred to herein as back telemetry data.

Electrode lead 408 may be implemented in any suitable manner. For example, a distal portion of electrode lead 408 may be pre-curved such that electrode lead 408 conforms with the helical shape of the cochlea after being implanted. Electrode lead 408 may alternatively be naturally straight or of any other suitable configuration. In some examples, electrode lead 408 includes a plurality of wires (e.g., within an outer sheath) that conductively couple electrodes 410 to one or more current sources within cochlear implant 204. For example, if there are n electrodes 410 on electrode lead 408 and n current sources within cochlear implant 204, there may be n separate wires within electrode lead 408 that are configured to conductively connect each electrode 410 to a different one of the n current sources. Illustrative values for n may include 8, 12, 16, or any other suitable integer as may serve a particular implementation.

Electrodes 410 are located on at least a distal portion of electrode lead 408. In this configuration, after the distal portion of electrode lead 408 is inserted into the cochlea of the recipient, electrical stimulation may be applied by way of one or more of electrodes 410 to one or more intracochlear locations. One or more other electrodes (e.g., including a ground electrode, not explicitly shown) may also be disposed on other parts of electrode lead 408 (e.g., on a proximal portion of electrode lead 408) to, for example, provide a current return path for stimulation current applied by electrodes 410 and to remain external to the cochlea after the distal portion of electrode lead 408 is inserted into the cochlea. Additionally or alternatively, a housing of cochlear implant 204 may serve as a ground electrode for stimulation current applied by electrodes 410.

Sound processor 402 may be configured to interface with (e.g., control and/or receive data from) cochlear implant 204. For example, sound processor 402 may transmit commands (e.g., stimulation parameters and/or other types of operating parameters in the form of data words included in a forward telemetry sequence) to cochlear implant 204 by way of the same communication link on which RF power 206 is shown to be transmitted. For example, the data words may be modulated onto RF power 206 in certain examples. RF power 206 generated by sound processor 402 may provide operating power to cochlear implant 204, as described above. The communication link carrying RF power 206 and any data communications (e.g., forward and backward telemetry communications) between sound processor 402 and cochlear implant 204 may be implemented by any suitable number of wired and/or wireless bidirectional and/or unidirectional links. For example, as will be described in more detail below, the communication link may be implemented as an inductive link between coils within headpiece 406 and cochlear implant 204.

Sound processor 402 may be configured to perform various operations with respect to cochlear implant 204 (e.g., by executing instructions stored in memory within sound processor 402). For instance, sound processor 402 may be configured to control operation of cochlear implant 204 by receiving an audio signal (e.g., by way of audio input 404), processing the audio signal in accordance with a sound processing program (e.g., a sound processing program stored in memory) to generate appropriate stimulation parameters, and then transmitting the stimulation parameters to cochlear implant 204 to direct cochlear implant 204 to apply electrical stimulation representative of the audio signal to the recipient.

In some implementations, sound processor 402 may also be configured to apply acoustic stimulation to the recipient. For example, in an electroacoustic hearing system implementation of cochlear implant system 400, an acoustic receiver (also referred to as a loudspeaker) may be optionally coupled to sound processor 402 (not shown in FIG. 4). In this configuration, sound processor 402 may deliver acoustic stimulation to the recipient by way of the receiver. The acoustic stimulation may be representative of an audio signal (e.g., an amplified version of the audio signal), configured to elicit an evoked response within the recipient. In examples in which sound processor 402 is configured to both deliver acoustic stimulation to the recipient and direct cochlear implant 204 to apply electrical stimulation to the recipient, cochlear implant system 400 may be referred to as an electroacoustic hearing system or another suitable term.

Sound processor 402 may be additionally or alternatively configured to receive and process data generated by cochlear implant 204. For example, sound processor 402 may receive data representative of a signal recorded by cochlear implant 204 using one or more electrodes 410 and, based on the data, may adjust one or more operating parameters of sound processor 402. Additionally or alternatively, sound processor 402 may use the data to perform one or more diagnostic operations with respect to cochlear implant 204 and/or the recipient. Other operations may be performed by sound processor 402 as may serve a particular implementation.

Sound processor 402 may be implemented by any suitable device that may be worn or carried by the recipient. For example, sound processor 402 may be implemented by a behind-the-ear ("BTE") unit configured to be worn behind and/or on top of an ear of the recipient. Additionally or alternatively, sound processor 402 may be implemented by an off-the-ear unit (also referred to as a body worn device) configured to be worn or carried by the recipient away from the ear. In some examples, at least a portion of sound processor 402 may be implemented by circuitry within headpiece 406. In some cases, sound processor 402 and headpiece 406 may be fully integrated into a single device rather than as separate devices as shown in FIG. 4.

Headpiece 406 may be selectively and communicatively coupled to sound processor 402 by way of a communication link implemented by a cable or any other suitable wired or wireless communication link. Headpiece 406 may be implemented in any suitable manner to facilitate communication between sound processor 402 and cochlear implant 204. For instance, headpiece 406 may include an external antenna (e.g., a coil and/or one or more wireless communication components) configured to facilitate selective wireless coupling of sound processor 402 to cochlear implant 204. Headpiece 406 may additionally or alternatively be used to selectively and wirelessly couple any other external device to cochlear implant 204. To this end, headpiece 406 may be configured to be affixed to the recipient's head (e.g., by way of a magnet, a hair clip, etc.) and positioned such that the external antenna housed within headpiece 406 becomes aligned with a corresponding implantable antenna (which may also be implemented by a coil and/or one or more wireless communication components) included within or otherwise connected to cochlear implant 204. In this manner, communicative lock between sound processor 402 and cochlear implant 204 may be achieved and stimulation parameters and/or RF power may be wirelessly and transcutaneously transmitted between sound processor 402 and cochlear implant 204 by way of headpiece 406.

Audio input 404 may provide, to sound processor 402, an audio signal representative of audio content to be conveyed to the recipient. As described above, sound processor 402 may communicate data representative of this audio signal to cochlear implant 204 by way of headpiece 406. In this way, sound processor 402 may direct cochlear implant 204 to apply electrical stimulation representative of the audio signal to the recipient (e.g., by way of current applied via electrodes 410 on electrode lead 408, as described above). The audio signal provided by audio input 404 may include or otherwise be representative of any suitable audio content that is to be conveyed to the recipient.

Figure 5:
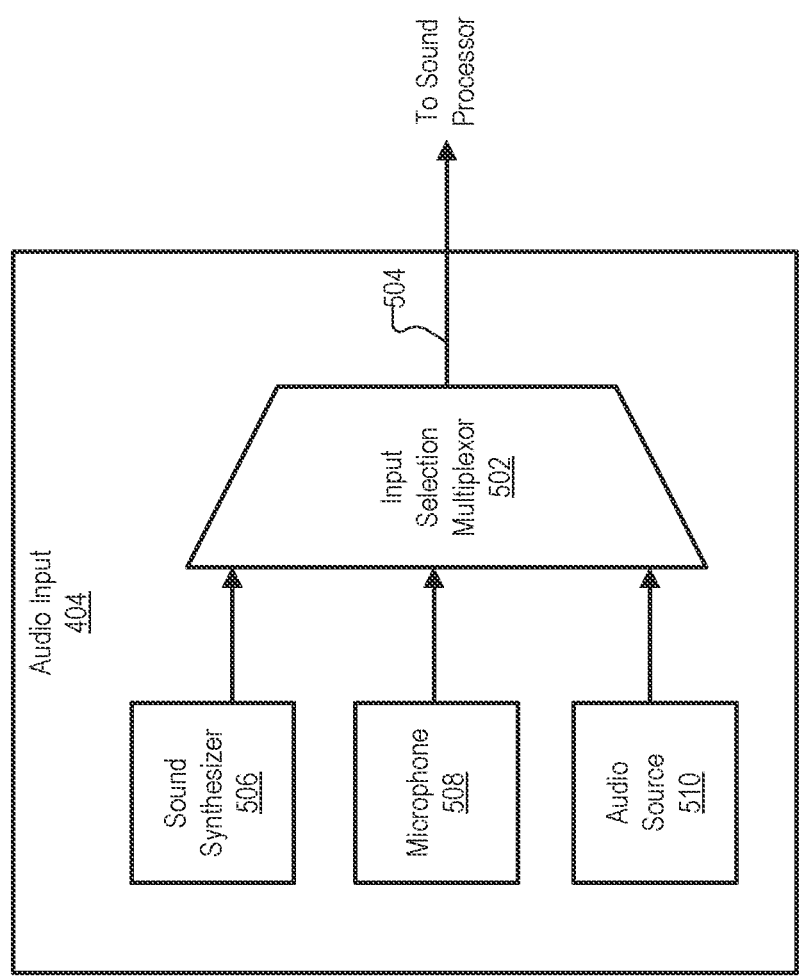
FIG. 5 shows illustrative aspects of potential audio input that may be delivered to the cochlear implant system of FIG. 4.

To illustrate, FIG. 5 shows illustrative aspects of a potential implementation of audio input 404 that may be delivered to cochlear implant 204. Specifically, as shown, audio input 404 may include an input selection multiplexor 502 that outputs, to sound processor 402 as an audio signal 504, audio content from at least one of a sound synthesizer 506, a microphone 508, or an audio source 510 of a recording (e.g., music, a spoken word recording, etc.) or other audio file or stream.

Input selection multiplexor 502 may be implemented in any way as may serve a particular implementation to allow for selection of audio input from the different input sources as the recipient may desire. In some examples, a combination of two or more of the input signals may be combined within input selection multiplexor 502 to form audio signal 504. While illustrated within audio input 404 as a device or circuit that is separate from and communicatively coupled to sound processor 402, it will be understood that input selection multiplexor 502 may, in certain implementations, be integrated with sound processor 402 (e.g., built into the sound processor) and at least some of the input audio sources (e.g., sound synthesizer 506, microphone 508, etc.) may also be integrated with sound processor 402.

In certain circumstances, the audio content represented by audio signal 504 may include synthesized sounds such as tones used for calibration, fitting, or other purposes. To this end, sound synthesizer 506 may generate sound from scratch rather than for example, by capturing the sound (as microphone 508 may do) or playing back sound that has been previously captured and recorded (as audio source 510 may do). Sound synthesizer 506 may generate tones at different frequencies as may be called for by a system calibration mode (e.g., in examples in which the power calibration or other types of calibration are performed at startup or other phases of an operating session), a fitting session in which the cochlear implant system is optimized to the particular recipient, or the like.

In other circumstances, the audio content represented by audio signal 504 may include environmental sound captured, while the processor operates in the power adaptation mode, by a microphone worn by the recipient or otherwise placed near sound that the recipient desires to hear. To this end, microphone 508 may be configured to detect one or more audio signals (e.g., that include speech and/or any other type of sound) in an environment of the recipient and may be implemented in any suitable manner. For example, microphone 508 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 402. Additionally or alternatively, microphone 508 may be implemented by one or more microphones in or on headpiece 406, one or more microphones in or on a housing of sound processor 402, one or more beam-forming microphones, and/or any other suitable microphone as may serve a particular implementation. Microphone 508 may also represent a probe microphone disposed in an ear tip at the ear canal (e.g., used to monitor sound presented to the recipient at the ear canal), a microphone not worn by the recipient but placed elsewhere in the room (e.g., placed near a person speaking at a conference, worn by a companion of the recipient in a noisy restaurant, etc.), or any other suitable microphone or set of microphones placed at any suitable location as may serve a particular implementation.

In still other circumstances, audio signal 504 may be provided to sound processor 402 by an audio source communicatively coupled to the processor. For example, a music player or other mobile device may be communicatively coupled to sound processor 402 by way of a cable or wireless interface (e.g., a Bluetooth interface or the like) such that a phone call or prerecorded sound (e.g., music, a spoken word recording, etc.) may be played back or streamed directly to the recipient by way of the cochlear implant system.

While sound synthesizer 506 may generate sounds specifically applied to the cochlear implant for purposes other than facilitating the sense of hearing for the recipient (e.g., for system calibration, fitting, or other purposes), audio content associated with microphone 508 and/or audio source 510 may each be considered "natural sounds" that are desired to be heard by the recipient during normal operation of the cochlear implant system (e.g., during normal day-to-day activities of the recipient). As has been mentioned and as will be described below in more detail, various benefits may arise from systems and methods herein that simplify or entirely bypass a conventional power calibration procedure and instead perform runtime adaptive RF power control for the cochlear implant system based on natural sounds such as generated by microphone 508 and/or audio source 510.

Returning to FIG. 4, an illustrative computing device 412 is configured to communicatively couple to sound processor 402 by way of any suitable wired or wireless communication link. Computing device 412 may be implemented by any suitable combination of hardware and software. To illustrate, computing device 412 may be implemented by a mobile device (e.g., a mobile phone, a laptop, a tablet computer, etc.), a desktop computer, and/or any other suitable computing device as may serve a particular implementation. As an example, computing device 412 may be implemented by a mobile device configured to execute an application (e.g., a "mobile app") that may be used by a user (e.g., the recipient, a clinician, and/or any other user) to control one or more settings of sound processor 402 and/or cochlear implant 204 and/or perform one or more operations (e.g., diagnostic operations) with respect to data generated by sound processor 402 and/or cochlear implant 204.

In some examples, computing device 412 may be configured to control an operation of cochlear implant 204 by transmitting one or more commands to cochlear implant 204 by way of sound processor 402. Likewise, computing device 412 may be configured to receive data generated by cochlear implant 204 by way of sound processor 402. Alternatively, computing device 412 may interface with (e.g., control and/or receive data from) cochlear implant 204 directly by way of a wireless communication link between computing device 412 and cochlear implant 204. In some implementations in which computing device 412 interfaces directly with cochlear implant 204, sound processor 402 may or may not be included in cochlear implant system 400.

Computing device 412 is shown as having an integrated display 414. Display 414 may be implemented by a display screen, for example, and may be configured to display content generated by computing device 412. Additionally or alternatively, computing device 412 may be communicatively coupled to an external display device (not shown) configured to display the content generated by computing device 412.

In some examples, computing device 412 represents a fitting device configured to be selectively used (e.g., by a clinician) to fit sound processor 402 and/or cochlear implant 204 to the recipient. In these examples, sound synthesizer 506 may be integrated with computing device 412 and computing device 412 may be configured to execute a fitting program configured to set one or more operating parameters of sound processor 402 and/or cochlear implant 204 to values that are optimized for the recipient. As such, in these examples, computing device 412 may not be considered to be part of cochlear implant system 400. Instead, computing device 412 may be considered to be separate from cochlear implant system 400 such that computing device 412 may be selectively coupled to cochlear implant system 400 when it is desired to fit sound processor 402 and/or cochlear implant 204 to the recipient.

Figure 6:
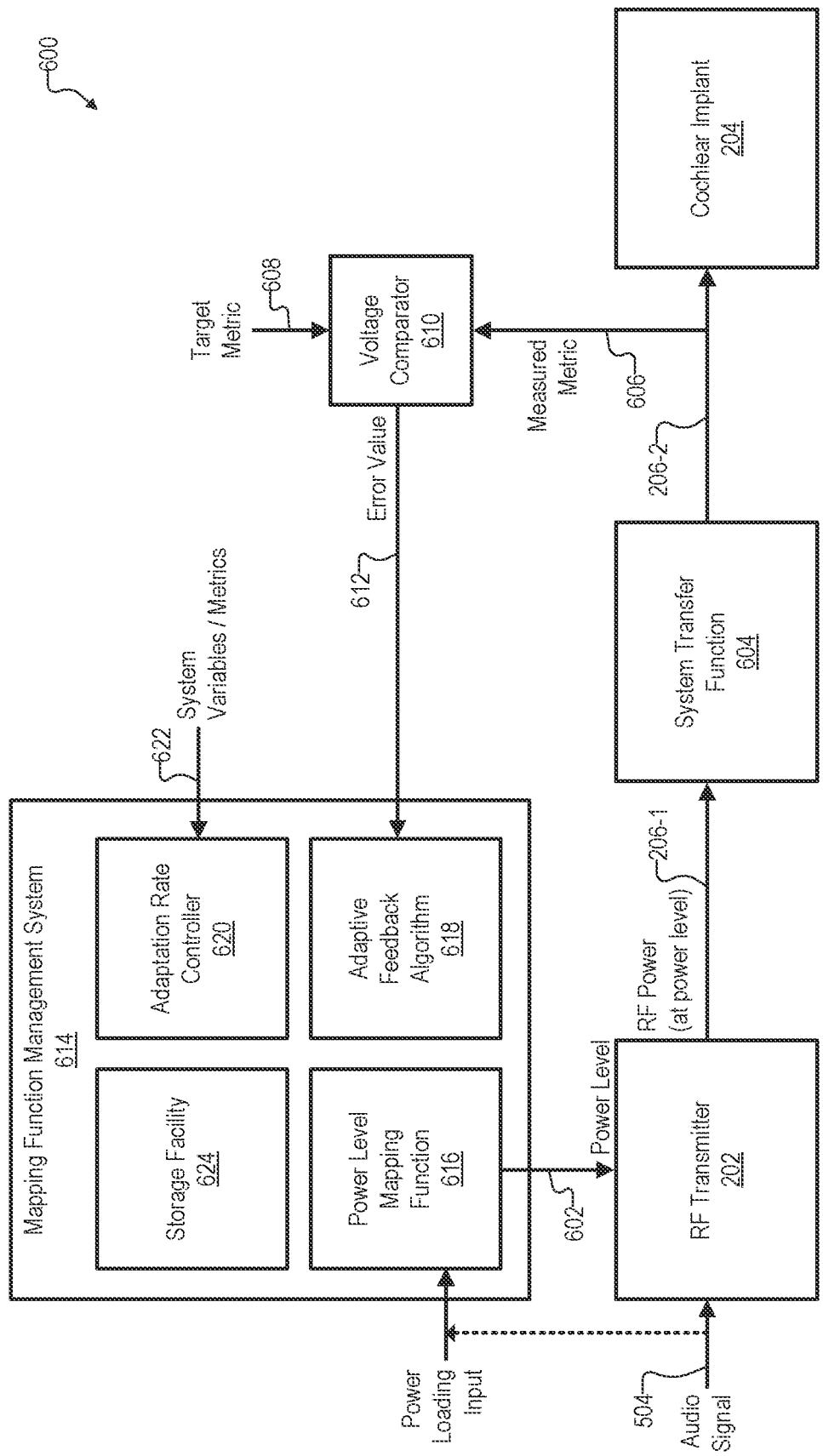
FIG. 6 shows an illustrative block diagram of how an RF power control system may operate to dynamically control a power level of an RF transmitter providing RF power to a cochlear implant.

FIG. 6 shows an illustrative block diagram 600 of how an RF power control system (e.g., system 100, system 200, an implementation thereof, etc.) may operate to dynamically control a power level of an RF transmitter providing RF power to a cochlear implant (e.g., performing method 300 within a configuration such as illustrated by cochlear implant system 400). As shown, RF transmitter 202 may take, as input, both audio signal 504 (which may include audio content from any of the input signals of audio input 404 described above and/or other suitable audio content) and a power level 602. Based on these inputs, RF transmitter 202 may generate RF power 206 at the particular power level indicated by power level 602. More particularly, the RF power 206 generated at RF transmitter 202 is labeled as RF power 206-1 to distinguish this RF power (and its corresponding power level) from RF power 206-2, which may have an attenuated power level due to the RF power having traversed a system transfer function 604 that includes, for example, the transcutaneous transmission by headpiece 406, filtering and conversion of the RF power by power input circuitry of cochlear implant 204, and so forth.

A measured metric 606 (e.g., a supply voltage received by cochlear implant 204 and measured by data processing circuitry of the cochlear implant after power supply circuitry has filtered RF power 206 or another suitable metric) is detected at cochlear implant 204 and compared to a target metric 608 at a voltage comparator 610 to generate an error value 612. A mapping function management system 614 is shown to include a power level mapping function 616, an adaptive feedback algorithm 618, an adaptation rate controller 620 informed by one or more system variables 622, and a storage facility 624. Mapping function management system 614 may serve as part of a feedback loop to generate power level 602 based on error value 612 and other inputs such as system variables 622 and a power loading input associated with audio signal 504 and/or other processed system variables such as described above. Certain components of block diagram 600 have been described above (e.g., RF transmitter 202, cochlear implant 204, RF power 206, etc.) and will be understood to perform the functions that have been described in the context of the example illustrated by block diagram 600. Each of the other signals and components illustrated in FIG. 6 will now be described in more detail with reference to FIG. 6, as well as with reference to FIGS. 7, 8, 9A, and 9B.

Power level 602 is determined by mapping function management system 614 based on power level mapping function 616, which, as has been mentioned and will be described and illustrated in more detail below, may be continuously and dynamically updated during operation of cochlear implant system 400 so as to initially define (if no dedicated calibration procedure is used), and/or dynamically refine (whether or not a dedicated calibration procedure is used), power level mapping function 616 to be accurate and up-to-date even as circumstances change during operation. Power level 602 represents a power level that may be stored, communicated, and implemented in any suitable way. For example, power level 602 may include an AC voltage value that is to be transmitted, modulation parameters affecting how data (e.g., stimulation parameters representative of audio signal 504) is to be modulated onto RF power 206 (and thereby how much power is actually delivered), and/or any other values or parameters as may serve a particular implementation. As will be described in more detail below, power level 602 may be determined based on power level mapping function 616, a power loading input that is based on audio signal 504 and/or other variables as have been described, and/or any of various system conditions as may exist at a particular moment in time.

System transfer function 604 represents a variety of cochlear implant system components and other related phenomena that will affect the RF power 206 as generated by RF transmitter 202 (i.e., RF power 206-1) and as finally received and used by cochlear implant 204 (i.e., RF power 206-2). For example, system transfer function 604 may depend on various hardware elements (e.g., the sound processor, an RF cable between the sound processor and the headpiece, the headpiece, a skin flap thickness, an orientation of coils on either side of the skin flap, the cochlear implant, etc.) and may represent, for example, the effect on RF power 206 of being transmitted through the RF cable connecting the RF transmitter to the headpiece (e.g., headpiece 406), being wirelessly transmitted by way of a coil in the headpiece, propagating through the skin flap of the recipient, being wirelessly received by a coil implanted within the recipient, being filtered and processed (e.g., converted from AC to DC power, etc.) by power circuitry associated with cochlear implant 204, and ultimately arriving at a supply power input to circuitry of cochlear implant 204. Because many steps along this chain represented by system transfer function 604 may be difficult to predict for different recipients and may even be subject to dynamically change, the transfer function may be different from setup to setup and it may not be possible or practical to define system transfer function 604 as a static transfer function prior to runtime. Moreover, the amount of power used by cochlear implant 204 may dynamically change based on various system conditions (e.g., when the headpiece orientation or coil alignment changes due to slight movements or readjustments of the headpiece by the recipient, etc.). Accordingly, system transfer function 604 may be thought of as a constantly-evolving relationship between power being provided externally and power being used internally. A high-level objective of the feedback loop represented in block diagram 600 is thus to adaptively model and react to that relationship as it changes.

Measured metric 606 may be detected within cochlear implant 204 or at another suitable point in the signal chain as any suitable metric that can help quantify the effect of system transfer function 604, the difference between RF power 206-1 and RF power 206-2, the power level actually delivered to cochlear implant 204, or the like. For example, measured metric 606 may represent a voltage that is actually being supplied to cochlear implant 204 at a given moment. For example, measured metric 606 may be implemented as a measured tank voltage for cochlear implant 204 or another indicator that, when compared to a supply target, helps reveal whether (or the extent to which) a proper amount of power (e.g., sufficient power without being overly inefficient) is being provided. Other examples of metrics that can be used for measured metric 606 to this end (in addition or as alternatives to detected supply or tank voltages) include reflected power to RF transmitter 202, real or imaginary impedance from RF transmitter 202, impedance discontinuities (e.g., stationary or transient discontinuities) that are in the circuit naturally around the set-point or forced intentionally to provide an indication to the speech processor, power consumption of cochlear implant 204, indications of a threshold violation related to the supply voltage to cochlear implant 204, stimulation current being applied by cochlear implant 204, DAC compliance voltage violations measured at cochlear implant 204, and/or any other such real-time indicators of power actually needed and/or used by cochlear implant 204. Depending on the algorithm implementing adaptive feedback algorithm 618 and/or other factors, measured metric 606 may be implemented as an instantaneous voltage or an average over a moving window of time.

Target metric 608 may represent the same type of metric as measured metric 606, but rather than being a sampled or measured value, may be an ideal value (e.g., a desired value by a designer of the cochlear implant system for a given stimulation strategy). For example, if measured metric 606 is a tank voltage for cochlear implant 204, target metric 608 may be a target tank voltage that, when achieved, correlates with proper operation of cochlear implant 204 (e.g., fully functional operation in which stimulation is provided at a desired intensity level, the dynamic range of audio signal 504 is properly represented, lock between RF transmitter 202 and cochlear implant 204 is maintained, etc.). In some examples, target metric 608 may be implemented by a static or relatively static value (e.g., a supply voltage that particular circuitry within cochlear implant 204 is designed to always receive), while, in other examples, target metric 608 may be implemented by a more dynamic (e.g., compliance-based) value driven by a more complex RF power control strategy. This would involve determining a compliance voltage that is needed on the fly using stimulation data and patient impedance values.

Voltage comparator 610 may include any circuitry configured to compare measured metric 606 and target metric 608 to generate an error value 612 representative of the difference between the actual measured metric 606 and the ideal target metric 608. Since the objective may be to keep measured metric 606 equal to target metric 608, it may be desirable for error value 612 to stay at or near zero, and any meaningful deviation from zero for error value 612 may be indicative of changes that need to be made to power level mapping function 616 (and therefore to power level 602 that RF transmitter 202 is being directed to transmit).

Figure 7:
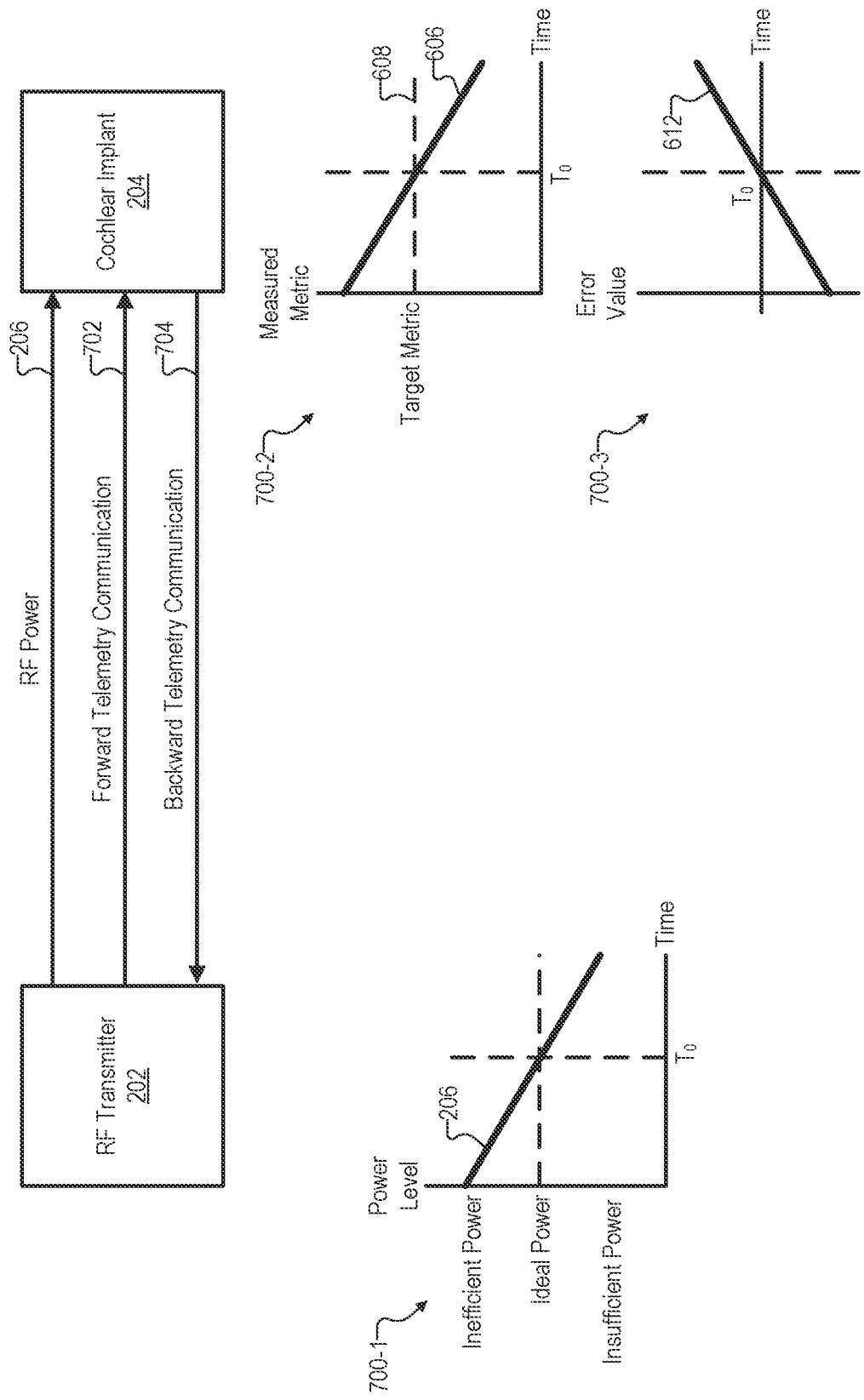
FIG. 7 shows illustrative aspects of transcutaneous power transmission and communication in a cochlear implant system in which an RF power control system is implemented.

To further illustrate the interplay between some of these elements, FIG. 7 shows certain aspects of transcutaneous power transmission and communication in a cochlear implant system in which an RF power control system such as system 100 or 200 is implemented. Three graphs 700 (i.e., graphs 700-1 through 700-3) are shown in FIG. 7 to illustrate certain values associated with the components (e.g., RF transmitter 202 or cochlear implant 204) where the values are generated or measured. It will be understood that the values in all of graphs 700 are shown for a specific arbitrary example with respect to a same timeline.

Specifically, in this example, a first graph 700-1 associated with RF transmitter 202 (i.e., drawn under RF transmitter 202) illustrates the RF power 206 generated by RF transmitter 202 as having a power level that is more than sufficient to supply cochlear implant 204 at a first time and thus may be wasteful or inefficient (indicated by being above a dashed line labeled "Ideal Power" in a region labeled "Inefficient Power") and linearly ramping down to a power level that is not sufficient to properly supply cochlear implant 204 at a second time (indicated by being below the dashed line labeled "Ideal Power" in a region labeled "Insufficient Power"). At a time $T_0$, RF power 206 is shown in this example to be precisely at the threshold where the power is deemed to be ideal (i.e., sufficient but is not more than is needed). As such, while the Ideal Power level may be a moving target that is unknown by RF transmitter 202 in practice, it will be understood that the objective of the RF power control system is to determine and maintain RF power 206 at a power level as close as possible to the Ideal Power dashed line as possible.

Graph 700-2 shows measured metric 606 as detected at cochlear implant 204 for the example in which RF power 206 is ramping down over time as shown in graph 700-1. Graph 700-2 also shows a static value for target metric 608 that is being used for this example (illustrated as a dashed line labeled "Target Metric"). Unlike the theoretical Ideal Power line shown in graph 700-1, which is not actually known to RF transmitter 202, the target metric 608 represented by the Target Metric line in graph 700-2 is known to the system. As illustrated, when RF transmitter 202 is providing more than sufficient power so as to not be operating as efficiently as it otherwise might (i.e., up until time $T_0$ while RF power 206 is greater than the Ideal Power line in graph 700-1), graph 700-2 shows that measured metric 606 is greater than target metric 608. Additionally, once cochlear implant 204 consumes more power than is actually being supplied (i.e., after time $T_0$, when RF power 206 sinks below the Ideal Power line in graph 700-1), the measured metric 606 detected at cochlear implant 204 also begins to sink below target metric 608. Accordingly, it may be desirable to keep RF power 206 consistently at a power level such as the power level at time $T_0$, where measured metric 606 and target metric 608 are equal.

To implement this objective, graph 700-3 shows error value 612, which represents the difference between measured metric 606 and target metric 608. As shown, before $T_0$, when measured metric 606 is greater than target metric 608 (since RF power 206 is greater than the Ideal Power), error value 612 is less than zero to indicate that the power, while sufficient for proper operation, is being supplied inefficiently. However, as measured metric 606 passes target metric 608 at time $T_0$ (i.e., as the power level supplied to cochlear implant 204 becomes increasingly insufficient to power operations of cochlear implant 204), error value 612 is shown to increase above zero to indicate that the power, while not being used inefficiently, is now insufficient for powering proper operation of cochlear implant 204. Error value 612 may thus be used by mapping function management system 614 to help determine, refine, and maintain power level mapping function 616 that, when used to generate power level 602, ultimately creates a feedback look that facilitates keeping power level 602 at a level that is neither inefficient nor insufficient (such that error value 612 remains at a zero or near-zero value). It will be understood that the rising slope of error value 612 in graph 700-3 is a result of an arbitrary design choice to subtract measured metric 606 from target metric 608. However, it will be understood that an inverse (falling slope) version of error value 612 may be used in other implementations in which target metric 608 is instead subtracted from measured metric 606.

As has been mentioned, processor 104 of the RF power control system may be configured to operate external to the recipient (e.g., within RF transmitter 202) and to direct cochlear implant cochlear implant 204 by way of forward telemetry communication (e.g., communication indicative of stimulation that is to be applied to convey a sense of hearing to the recipient). This forward telemetry communication is shown with an arrow between RF transmitter 202 and cochlear implant 204 in FIG. 7 alongside the RF power 206 arrow and labeled forward telemetry communication 702. Also shown between RF transmitter 202 and cochlear implant 204 is an arrow labeled as backward telemetry communication 704. Backward telemetry communication 704 may be employed for any suitable purpose, including communicating the measured metric 606 detected at cochlear implant 204 (e.g., for an implementation in which sound processor 402 or another external device determines error value 612), communicating a precomputed error value 612 based on the measured metric 606 detected at cochlear implant 204 (e.g., for an implementation in which cochlear implant 204 performs the determining of error value 612), or communicating any other data as may serve a particular implementation.

For example, in an implementation in which cochlear implant 204 is configured to detect measured metric 606 and transmit (a precomputed) error value 612 or (the raw detected) measured metric 606 to an external processor 104, this communication may be performed by way of backward telemetry communication 704. In other words, the determining of error value 612 by processor 104 may comprise at least one of: 1) receiving error value 612 from cochlear implant 204 by way of backward telemetry communication 704; or 2) receiving the detected measured metric 606 from cochlear implant 204 by way of backward telemetry communication 704 and then calculating error value 612 based on the detected measured metric 606 that is received.

Returning to FIG. 6, error value 612 is provided to mapping function management system 614, which includes hardware and software configured to manage and ultimately apply a dynamic power level mapping function to power level 602 that is used by RF transmitter 202 to generate RF power 206-1 at a power level that will provide sufficient and efficient power to cochlear implant 204. More particularly, a model of what power level 602 is to be applied by RF transmitter 202 for different power needs of cochlear implant 204 is dynamically maintained as power level mapping function 616 for use by mapping function management system 614 to provide power level 602 to RF transmitter 202.

Inputs to power level mapping function 616 (labeled in FIG. 6 as "Power Loading Input") may include any suitable input or inputs as are described herein or as may serve a particular implementation. For example, certain inputs may be based on (e.g., may change dynamically with or otherwise correspond to) audio signal 504, as illustrated by the dotted line extending from audio signal 504 to the Power Loading Input. Other input may be based on other circumstances that the cochlear implant system may be under as stimulation is provided to the recipient. For example, as described above, certain variables incorporated into the Power Loading Input may be indicative of the stimulation load associated with audio signal 504, the extent to which back-telemetry and/or other housekeeping implant loads are to be accounted for, effects that an internal battery may have on the overall load if present (e.g., due to the battery charging, etc.), effects that a neural recording amplifier may have on the overall load if present, and so forth.

Regardless of which variables are accounted for in the Power Loading Input, the directing of RF transmitter 202 to provide RF power 206 to cochlear implant 204 at power level 602 may involve determining power level 602 based on power level mapping function 616 in any suitable way. As a first example, mapping function management system 614 may determine power level 602 by computing an average stimulation current used by cochlear implant 204 to apply the electrical stimulation for audio signal 504 and designating power level 602 to be an output of power level mapping function 616 when the detected average stimulation current is input into power level mapping function 616. As another example, mapping function management system 614 may determine power level 602 by sensing a power load imposed by cochlear implant 204 and designating power level 602 to be an output of power level mapping function 616 when the sensed power load is input into power level mapping function 616. As yet another example, mapping function management system 614 may determine power level 602 by detecting a characteristic of audio signal 504 and designating power level 602 to be an output of power level mapping function 616 when the detected characteristic of audio signal 504 is input into power level mapping function 616.

Figure 8:
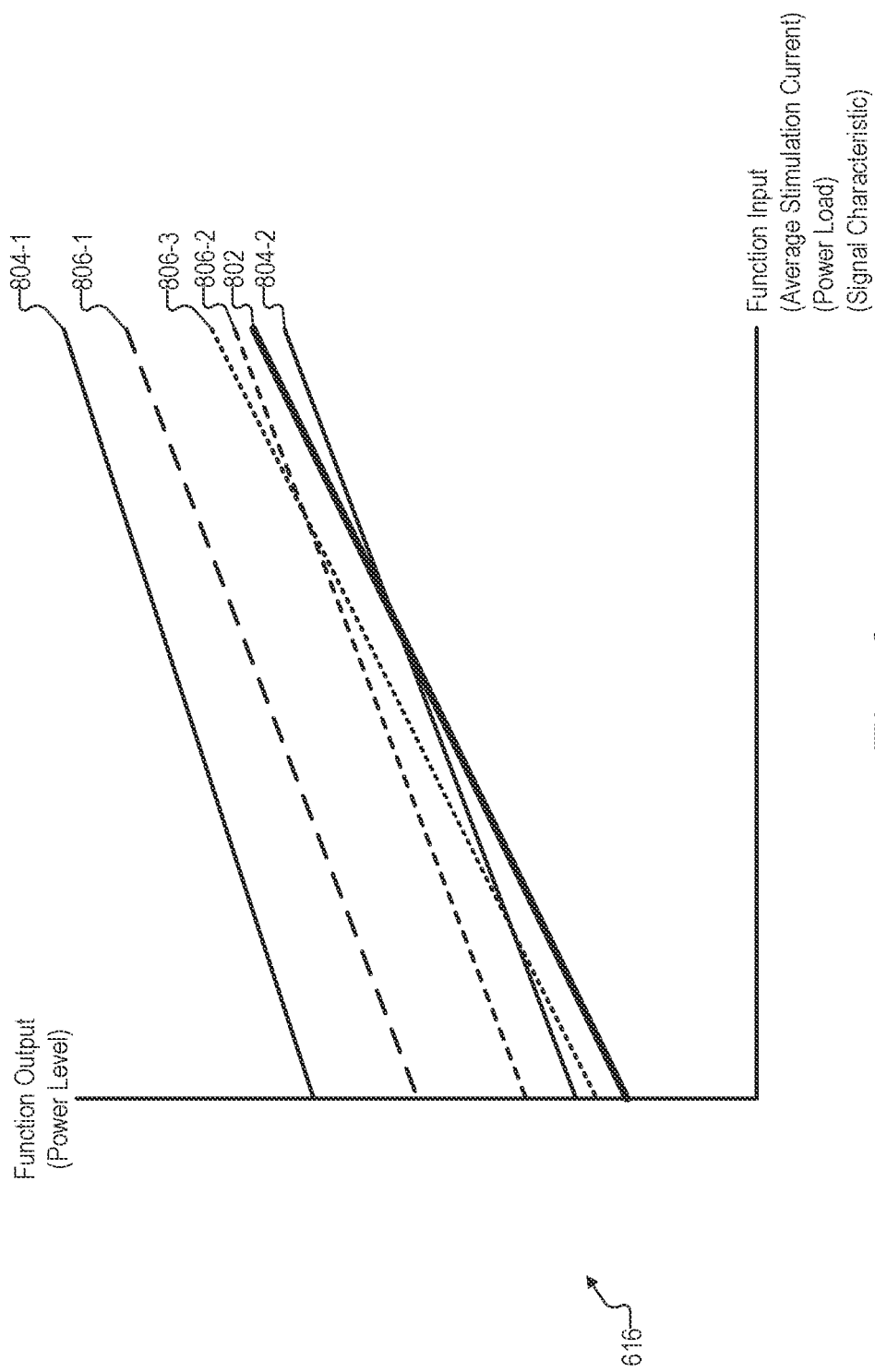
FIG. 8 shows illustrative linear power level mapping functions used to facilitate runtime adaptive RF power control for a cochlear implant.

To illustrate these examples, FIG. 8 shows various power level mapping functions 616 used to facilitate RF power control without calibration for a cochlear implant. More particularly, a power level mapping function 802 will be understood to represent a true or optimal power level mapping function that is unknown to mapping function management system 614, but which mapping function management system 614 is configured to progressively move toward with the presently-constituted power level mapping function 616. To this end, mapping function management system 614 may begin by initializing power level mapping function 616 to one of power level mapping functions 804 (e.g., power level mapping function 804-1 or 804-2 or another suitable initial function), and then may progress toward power level mapping function 802 by way of one or more intermediate power level mapping functions 806 (e.g., power level mapping functions 806-1 through 806-3 or other suitable intermediate functions between the initial power level mapping function 804 and the true power level mapping function 802).

Each of power level mapping functions 804 and 806 may be determined in any suitable way to be any suitable function that helps mapping function management system 614 ultimately move power level mapping function 616 toward the ideal of power level mapping function 802.

As one example, power level mapping function 804-1 may represent an implementation in which mapping function management system 614 initializes power level mapping function 616, prior to the updating of the power level mapping function, based on a predetermined function configured to cause power level 602 to be at least a maximum power level used by cochlear implant 204 to apply the electrical stimulation. In this example, power level mapping function 804-1 may represent a conservative power level mapping function that provides an amount of power that is guaranteed to be enough for proper functionality of cochlear implant 204, even if that comes at the expense of the greater efficiency that will be gained as power level mapping function 616 moves closer to power level mapping function 802. In other words, the predetermined function may be configured to cause the power level at which the RF power is provided to be at least the maximum power level used by the cochlear implant in any use-case scenario that may be anticipated. This predetermined function used for power level mapping function 804-1 may be stored in storage facility 624 or another suitable location and accessed and applied as a calibration-less starting point to set power level mapping function 616 relatively near the true function but in a way that is guaranteed not to sacrifice system functionality or quality as the power level mapping function is progressively adapted to be more and more efficient. In some examples, power level mapping function 804-1 may represent the predetermined function as it is stored, while in other examples, power level mapping function 804-1 may be based on the predetermined function by implementing an offset from the stored function or otherwise being derived from the stored function as may serve a particular implementation.

As another example, power level mapping function 804-2 may represent an implementation in which mapping function management system 614 initializes power level mapping function 616, prior to the updating of the power level mapping function, based on a previously-used function used and stored by the system (e.g., by mapping function management system 614 or another subsystem of system 100, system 200, or cochlear implant system 400) during a previous operating session in the power adaptation mode. For example, if in a previous operating session of cochlear implant system 400, an implementation of the RF power control system (e.g., system 100 or 200) ultimately arrived at power level mapping function 804-2, power level mapping function 804-2 may be used as a calibration-less starting point to set power level mapping function 616 relatively near the true function in a way that is likely to provide sufficient power at most values of the function input while being more efficient than the conservative starting point of power level mapping function 804-1. Similarly as described above with respect to power level mapping function 804-1, power level mapping function 804-2 may represent the previously-used function exactly as it is stored and/or was used during the previous operating session. Alternatively, power level mapping function 804-2 may be based on the previously-used function by implementing an offset from the function as stored (e.g., to avoid risk of underpowering the cochlear implant by making the initialized function slightly more conservative than the function as it was finally used during the previous operating session) or by otherwise being derived from the previously-used function as may serve a particular implementation.

As yet another example, either of power level mapping functions 804-1 or 804-2 may represent an initial calibrated power level mapping function generated within a mixed implementation in which mapping function management system 614 operates, prior to operating in the power adaptation mode, in a calibration mode (e.g., a dedicated calibration mode such as has been described herein). During the calibration mode, the system may perform a dedicated calibration procedure to determine the initial calibrated power level mapping function. In this type of implementation, mapping function management system 614 may initialize power level mapping function 616, prior to the updating of the power level mapping function, based on the initial calibrated power level mapping function determined as part of the dedicated calibration procedure in the calibration mode. For example, as has been described, a full-fledged calibration procedure may be performed to initialize the power level mapping function in some implementations (thereby forgoing some of the benefits associated with simplifying or eliminating the calibration procedure but still enjoying various other benefits described herein for run-time adaptive RF power control that can adapt to changing system circumstances). In other implementations, a simplified (e.g., abbreviated, rudimentary, streamlined, etc.) version of the calibration procedure may be employed in which the power level mapping function is determined with an emphasis on speed and efficiency rather than accuracy and precision. Similarly as described above, the initialized power level mapping function in this example (i.e., power level mapping function 804-1 or 804-2) may represent the initial calibrated power level mapping function either exactly as it is calibrated or as it may be otherwise derived (e.g., by adding or taking away an offset, etc.) from the initial calibrated power level mapping function.

Each of intermediate power level mapping functions 806 will be understood to represent potential waypoints at which power level mapping function 616 may be set between the starting point of a particular initial power level mapping function 804 and the targeted final destination of power level mapping function 802. For example, if starting from power level mapping function 804-1, mapping function management system 614 may update power level mapping function 616 progressively to power level mapping functions 806-1, 806-2, 806-3, and finally to a power level mapping function modeled after power level mapping function 802. In some examples, the progressive adjustments from power level mapping function 804-1 to the terminal power level mapping function (which should be similar to true power level mapping function 802 in this example) may utilize a phased target supply voltage ramp-down. That is, for examples in which there is no calibration at the beginning of a session, the starting values of slope and offset parameters may be high enough to be sufficient across all possible variations that may be encountered (e.g., various skin flap thicknesses, cable length combinations, etc.). These starting slope-offset parameters may be relatively high for most use cases, and as the parameters are adapted independently based on the function input, the system could end up overshooting the true function (i.e., having a significant amount of overcompensation) if care is not taken. Accordingly, to prevent this, the run-time adaptive RF power control algorithm may decrease parameters in relatively small steps (so as to gradually approach the true parameters and not overshoot them) and, after each adjustment is made, the algorithm may attempt to maintain the current parameters for some duration of time before continuing with additional adjustments. For example, the current parameters may be maintained for an amount of time that is inversely proportional to the variation of the average current.

The overshooting and/or undershooting of the power level mapping function as the system updates it may be associated with model overfitting that can occur when the system receives stimulation data over a very limited range (e.g., when there is a significant lack of diversity in stimulation). By adding wait-states at intermediate steps, the run-time adaptive RF power control algorithm may be provided more time to observe diverse stimulation data and correct any developed overfitting errors. Moreover, carefully imposing such wait times may lead to other benefits as well. For example, the system may be more able to correct small overcompensations that could have been created during each small step, there may be little overcompensation by the time the algorithm sets a final power level mapping function, and the risk of failure that may result from overcompensation (e.g., because power level 602 is reduced so far as to be insufficient for maintaining lock and/or proper functionality of cochlear implant 204) may be minimized or virtually eliminated.

In contrast, if starting from power level mapping function 804-2, mapping function management system 614 may update power level mapping function 616 to power level mapping function 806-3 (or another function that is similar to power level mapping function 802) before arriving at power level mapping function 802. In some examples, depending on the starting point of power level mapping function 804-2, similar overcompensation protection techniques may be employed in this type of implementation for similar reasons.

As shown, the y-axis representing the output ("Function Output") of each of the power level mapping functions illustrated in FIG. 8 may be a power level such as can be applied by RF transmitter 202 in the generation of RF power 206. Furthermore, as mentioned above, the x-axis representing the input ("Function Input") of each power level mapping function may be implemented as any of several variables that may be known by mapping function management system 614 so as to be entered into power level mapping function 616 as presently constituted to determine a desirable power level 602 for the present conditions. For example, as shown, the function input may be average stimulation current being consumed by cochlear implant 204 (e.g., as computed by the external processor by analyzing outgoing stimulation sent over forward telemetry communication 702, as indicated by cochlear implant 204 by way of backward telemetry communication 704, or in other suitable ways). As another example, the function input may be a power load that cochlear implant 204 is detected to put on RF transmitter 202. As yet another example, the function input may be based on a signal characteristic of audio signal 504 such as a volume or sound intensity of audio signal 504. These or other such characteristics may be advantageous function inputs since they may be closely correlated with the average stimulation current and/or power load imposed by cochlear implant 204 while not necessarily requiring communication (e.g., backward telemetry communication) from cochlear implant 204 to detect.

Each of the power level mapping function examples illustrated in FIG. 8 is shown to be a linear function that can be defined by a slope parameter and an offset parameter within the coordinate space of the function input (x-axis) and function output (y-axis). The parameterization of the power level mapping function as two parameter values (i.e., slope and offset parameters) may make for an efficient and convenient form of modeling for certain implementations, particularly when the true model (i.e., power level mapping function 802 in this example) has a more or less linear shape that can be represented using just these parameters. For instance, in these implementations, either or both of the slope and offset parameters may be progressively updated (e.g., using adaptive control techniques and algorithms such as well be described in more detail below) to more closely conform with the true model as the true model is gradually revealed by different error values 612 generated for different characteristics of audio signal 504.

In other examples, power level mapping functions implementations may be non-linear, segmented, and/or otherwise more complex than the linear implementations shown in FIG. 8. For instance, instead of being linear, a power level mapping function 616 may incorporate a piecewise-defined function including a plurality of continuous or discontinuous linear sub-functions, a plurality of continuous or discontinuous non-linear sub-functions, and/or other complexities (discontinuities, etc.) not explicitly represented in the examples of FIG. 8.

Figure 9A:
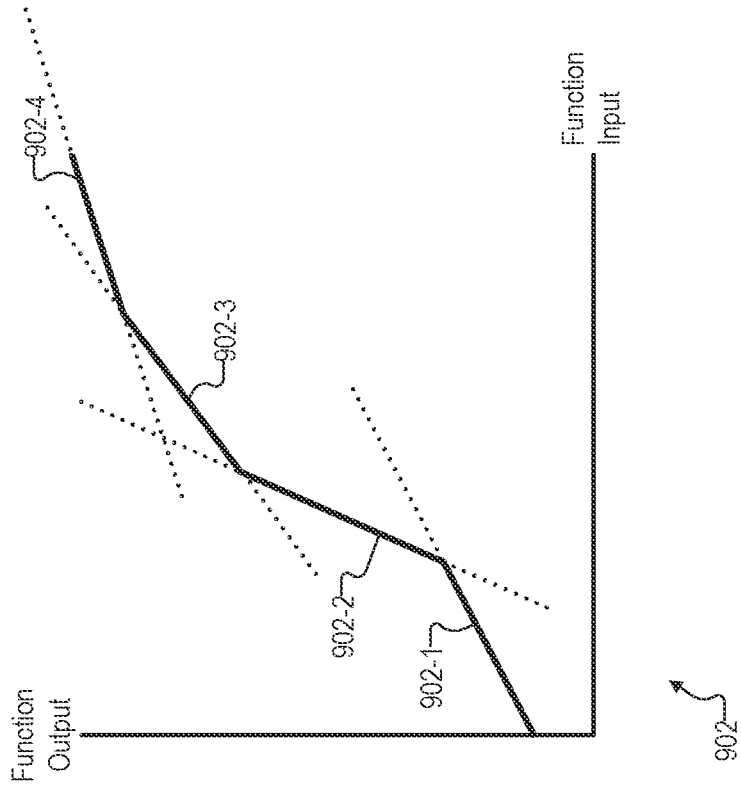
FIGS. 9A-9B show illustrative complex power level mapping functions used to facilitate runtime adaptive RF power control for a cochlear implant.
Figure 9B:
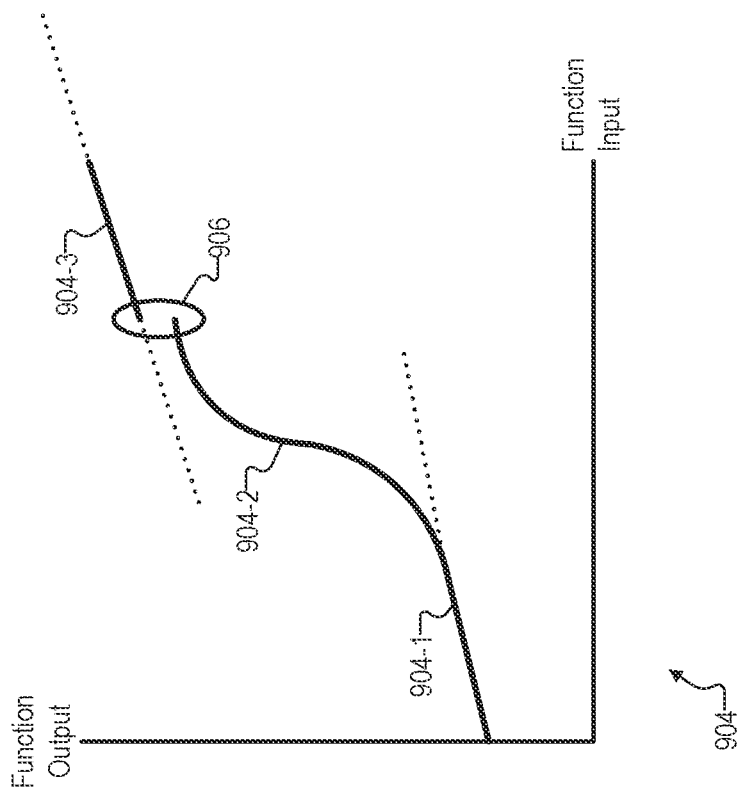

To illustrate, FIGS. 9A-9B show illustrative complex power level mapping functions used to facilitate runtime adaptive RF power control for a cochlear implant such as cochlear implant 204. More specifically, as shown, a power level mapping function 902 made up of a plurality of linear segments 902-1 through 902-4 is shown in FIG. 9A, while a non-linear and discontinuous power level mapping function 904 made up of a plurality of linear and non-linear segments 904-1 through 904-3, as well as a discontinuity 906, is shown in FIG. 9B. It will be understood that the power level mapping functions shown in FIGS. 9A and 9B are provided only by way of example, and that any type of linear, non-linear, continuous, discontinuous, disjointed, piecewise-defined, or other suitable function may serve as a power level mapping function in a particular implementation.

As shown by linear segments 902-1 through 902-4 of power level mapping function 902, as well as by linear segments 904-1 and 904-3 of power level mapping function 904, linear segments may be piecewise-defined over a portion of the function input (e.g., for a certain range of values on the x-axis) as part of a full line (illustrated by the segment itself and dotted-line extensions of the segment in FIGS. 9A and 9B). Each of these segments may be defined with its own slope and offset parameters such that the same types of algorithmic approaches used for linear power level mapping functions described above (e.g., Kalman filters, PID control loops, AI technologies, etc.) may be used on each segment. Segment boundaries between consecutive segments may be adjusted based on a weighted combination of boundaries predicted by the parameters of either segment. For example, a higher weight may be given to the segment that has been more confidently fleshed out (e.g., because the function input along that range has been present for more time such that that segment has had more time to adapt to the true model).

In some examples, a non-linear shape for a power level mapping function may be approximated using a piecewise-defined function such as shown in FIG. 9A and linear adaptive feedback algorithms may be used on each segment in a manner similar to described herein for linear power level mapping functions. In other examples such as shown in FIG. 9B, a non-linear function or non-linear segment of a function (e.g., non-linear segment 904-2) may be employed and adapted to in any suitable manner. Additionally, as illustrated in FIG. 9B, one or more discontinuities may be present within a power level mapping function such as illustrated by discontinuity 906 in power level mapping function 904.

Returning to FIG. 6, adaptive feedback algorithm 618 represents the modeling and/or self-learning techniques utilized by mapping function management system 614 to set, update, and/or otherwise manage power level mapping function 616 based on error value 612. Adaptive feedback algorithm 618 may enable the updating of power level mapping function 616 based on error value 612 in any suitable way and/or using any suitable techniques, mechanisms, control loops, mathematical or algorithmic constructs, or the like. For instance, the updating of power level mapping function 616 may be performed using a Kalman filter, a PID control loop or similar control loop mechanism, a least-mean-squares algorithm, an AI-based approach, or any other suitable algorithm or technology as may serve a particular implementation.

One role of adaptive feedback algorithm 618 may involve determining when to update and adapt power level mapping function 616, when to abstain from doing so, and when to accelerate or slow down the rate at which power level mapping function 616 is adjusted. For example, during the course of function adaptation, there may be various conditions that, if present, adaptive feedback algorithm 618 would be configured to slow down the adaptation rate or completely abstain from adapting and updating power level mapping function 616. Such conditions may include, for example: 1) when error value 612 is not being received or is determined to not be accurate; 2) when mapping function management system 614 is unable to provide the power level 602 prescribed by power level mapping function 616 (such that the feedback loop is temporarily broken); 3) due to limitations on the rate at which power level 602 can be changed based implant-specific circuitry that restricts the reduction of RF power so that a ramp-down procedure is gradual and controlled rather than immediate and abrupt (it is noted that the circuitry may or may not implement similar restrictions for immediate ramp-up of RF power); 4) when the average stimulation current or other function input is moving across two or more segments of a piecewise-defined power level mapping function (such that it becomes difficult to ascribe error value 612 to one of the segments of the piecewise-defined function and there is uncertainty about which segment parameters need to be adapted); or 5) when other conditions that create uncertainty or place limitations on the accuracy of the feedback loop mechanism are present.

Along with these and/or other conditions that may be accounted for when controlling the adaptation rate of the power level mapping function (including by abstaining from adapting the function), adaptive feedback algorithm 618 may also be informed by adaptation rate controller 620 about when conditions are such that effective learning and adaptation can take place, and when conditions are such that learning and adapting power level mapping function 616 may cause overcompensation or other such issues. Adaptation rate controller 620 may receive information (e.g., variables, metrics, etc.) labeled as system variables 622 in FIG. 6, and may use this information to determine the degree to which system operations merit adapting power level mapping function 616.

The updating of the power level mapping function may be performed at an update rate that adaptation rate controller 620 may be configured to determine based on one or more of system variable 622. These system variables may include, for example: a detected variance in electrical stimulation applied by the cochlear implant; a detected error in a feedback signal representative of the measured metric; a detected fluctuation, of an input into power level mapping function 616, between different sub-functions of the power level mapping function; a transit effect of the RF power; or another suitable variable representative of a particular real-time condition or circumstance. In this way, adaptation rate controller 620 may, as the update rate is determined, account for scenarios in which there is less variance in the recipient's electrical stimulation, scenarios in which there is an error in the feedback signal (e.g., an inaccurate implant supply voltage measurement due to hardware saturation), scenarios in which the recipient's electrical stimulation is fluctuating between consecutive segments of a piecewise-defined power level mapping function, scenarios in which the power level of 602 is in transit (i.e., in the process of changing) under power ramp-up and/or ramp-down restrictions that may be implemented, and so forth. In all of these and other scenarios, an objective of adaptation rate controller 620 may be to avoid model overfitting as well as model mislearning on erroneous samples.

In certain implementations, adaptation rate controller 620 may, based on an analysis of one or more of system variables 622 such as those described above, control the update rate used by adaptive feedback algorithm 618. For example, this may include increasing the update rate such that adaptive feedback algorithm 618 adjusts power level mapping function 616 at a relatively fast rate, decreasing the update rate such that adaptive feedback algorithm 618 adjusts power level mapping function 616 at a relatively slow rate, or pausing the updating altogether such that adaptive feedback algorithm 618 temporarily abstains from adjusting power level mapping function 616. In some scenarios, adaptation rate controller 620 may set the update rate at a relatively high level (e.g., implementing a "quick adaptation mode") in response to circumstances such as large negative errors occurring when the headpiece suddenly moves and thereby causes the previously-determined power level mapping function to be inaccurate and in need of quick readaptation. In other scenarios, adaptation rate controller 620 may set the update rate at a relatively low level or completely pause adaptation in response to other circumstances.

In implementations accounting for any of these types of scenarios, adaptive feedback algorithm 618 may, based on input from adaptation rate controller 620, account for an asymmetry in consequences for error value 612. For example, if error value 612 indicates that power level mapping function 616 is providing RF power 206 at too high a power level 602, the consequence may merely be that power is wasted (thereby shortening battery life, etc.). While this is certainly undesirable, this outcome may be far less consequential than the outcome when error value 612 indicates that power level mapping function 616 is providing RF power 206 at too low a power level 602 and cochlear implant 204 is at risk of operating incorrectly, losing lock, or the like. Accordingly, to address this asymmetry, adaptive feedback algorithm 618 may be configured to more aggressively and quickly make updates and adjustments that increase the power level 602 than to make updates and adjustments that would decrease the power level 602.

Storage facility 624 may store any suitable information used by mapping function management system 614. For example, storage facility 624 may store historical power level mapping functions that have been used under various circumstances (to be used as starting points for adaptation as described above or for error correction or other uses). As another example, storage facility 624 may store statistical information that is captured during operation of mapping function management system 614. Such information may be useful to produce improvements that account for the recorded statistics in the future.

Figure 10:
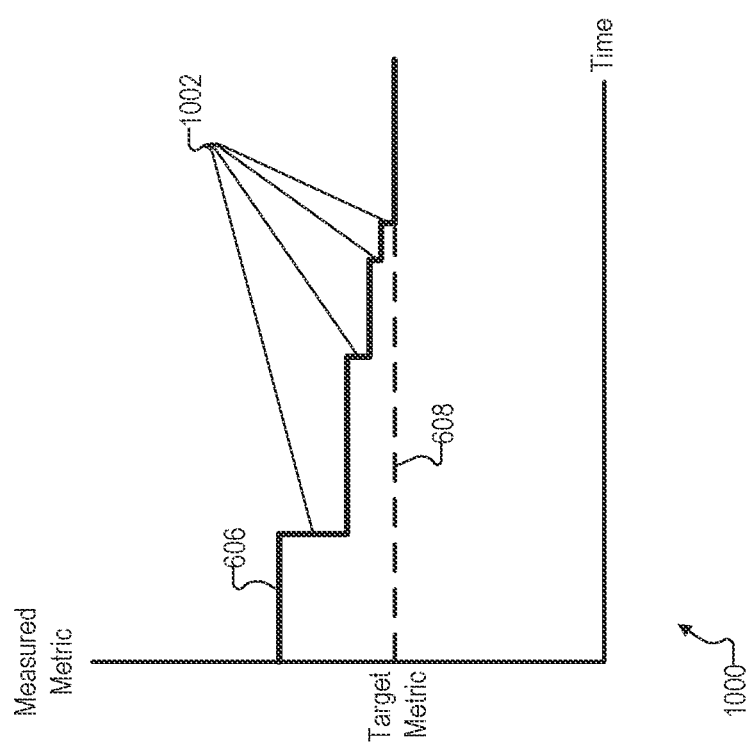
FIG. 10 shows how an illustrative supply voltage provided to the cochlear implant may converge over time toward a target supply voltage as a power level of transmitted RF power is updated by an RF power control system.

When block diagram 600 is implemented by an RF power control system such as system 100 or system 200, runtime adaptive RF power control may be performed for a cochlear implant of a cochlear implant system such as cochlear implant 204 of cochlear implant system 400. To illustrate an example of the supply voltage that may result from this power control, FIG. 10 shows how measured metric 606 provided to cochlear implant 204 may converge over time toward target metric 608 as power level 602 of transmitted RF power 206 is updated by the RF power control system (e.g., system 100 or an implementation thereof). While specific amounts of time are not indicated along the timeline of an x-axis of a graph 1000 shown in FIG. 10, it will be understood that measured metric 606 may converge to target metric 608 over the course of several seconds, minutes, or hours based on the characteristics and conditions of audio signal 504 and the system and how fast adaptive feedback algorithm 618 is configured to adapt power level mapping function 616 (as described in more detail above).

This process may involve several updates 1002 to power level mapping function 616 that are illustrated in graph 1000 by occasional stepwise changes to measured metric 606 that bring measured metric 606 into closer conformity with target metric 608. For example, measured metric 606 may be set at a value quite a bit higher than target metric 608 to ensure that there is plenty of power available to the system even if some amount of that will temporarily be wasted as the power level mapping function is progressively adapted. A first update 1002 may then be made after one minute of operation, a second update 1002 may be made after several more minutes of operation (when more natural sound has been applied to the recipient and additional data about how the power levels affect measured metric 606 at various different input values have been accounted for), and smaller additional updates 1002 may be made over the course of the next several minutes and hours as conditions continue to manifest themselves, as well as evolve and change.

Figure 11:
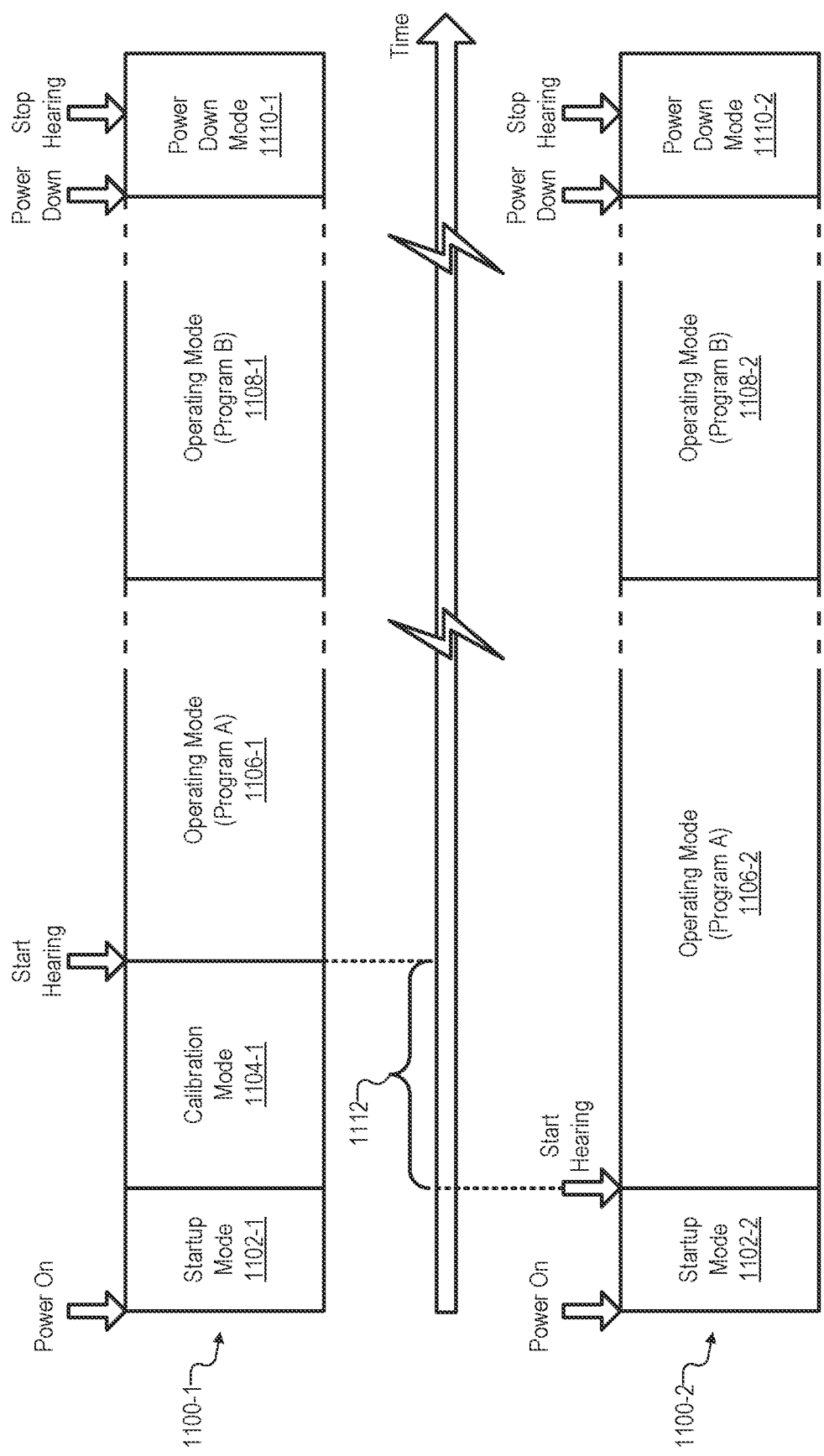
FIG. 11 shows certain timing aspects of two illustrative operating sessions for different cochlear implant systems.

FIG. 11 shows certain timing aspects of two illustrative operating sessions 1100 for different cochlear implant systems. More specifically, a session 1100-1 will be understood to take place on a cochlear implant system that employs a dedicated calibration procedure (e.g., either because the system is a mixed implementation or a conventional system that does not implement the power adaptation mode), while a session 1100-2 will be understood to take place on a cochlear implant system that bypasses the dedicated calibration procedure and exclusively relies on run-time adaptive RF power control described herein. As shown, both sessions 1100 are represented along a timeline ("Time") depicted as an arrow in between the session representations. Important events for each session are represented with small, labeled arrows above the session and varying modes of the cochlear implant system as the session progresses are indicated by boxes labeled 1102-1110, each of which includes a "-1" postfix for session 1100-1 or a "-2" postfix for session 1100-2.

As shown in the example of session 1100-1, a "Power On" event occurs to kick off session 1100-1 and to initialize a startup mode 1102-1 during which various system components and circuitry powers up and is properly initialized. This is followed by a calibration mode 1104-1 during which a dedicated calibration procedure (e.g., such as described above) is performed to determine, based on dedicated calibration sounds and stimulation (e.g., rather than natural sounds and operative stimulation), a power use model that will be used either for an initial calibrated power level mapping function (for a mixed implementation example) or for RF power control throughout the session (for a conventional example that does not implement runtime adaptive RF power control as described herein). Only once calibration mode 1104-1 is complete does normal stimulation begin for the recipient ("Start Hearing") as one of several non-calibration modes begin. Specifically, an operating mode 1106-1 begins that is based on a first sound processing program ("Program A") such as a sound processing program configured for use in the particular environment of the recipient (e.g., a quiet environment). At some point, the recipient may move to a different environment (e.g., a noisy environment instead of the quiet one) such that operating mode 1108-1 begins with use of a different sound processing program ("Program B"). Finally, at the end of session 1100-1 (e.g., at the end of the day, when the cochlear implant system needs to be charged, etc.), the recipient may indicate that the cochlear implant system is to be turned off ("Power Down"), and a power down mode 1110-1 is entered in which various components and circuitry are shut down and, at some point, stimulation ceases to be presented to the recipient ("Stop Hearing").

Similar to session 1100-1, session 1100-2 shows a startup mode 1102-2 that begins with a Power On event, two operating modes 1106-2 and 1108-2 (utilizing Program A and Program B, respectively) during which the recipient is presented with stimulation to convey a sense of hearing, and a power down mode 1110-2 that is initiated by a Power Down event and during which the recipient experiences the cessation of stimulation indicated as the Stop Hearing event. In contrast to session 1100-1, however, session 1100-2 shows that no calibration mode is used by the cochlear implant system providing session 1100-2 (indicated by the absence of any calibration mode 1104-2 in FIG. 11). Instead, as shown, the commencement of stimulation of natural sounds (e.g., the audio signal received by the microphone or other power adaptation sounds) indicated by the Start Hearing event is shown to occur directly after startup mode 1102-2 since no calibration mode need be performed.

As a result, a time differential 1112 on the timeline indicates a significant benefit of the application, by the second cochlear implant system, of the RF power control without calibration described herein. Specifically, rather than having to wait several additional seconds or longer for the calibration mode to be complete (as a recipient of the first cochlear implant system must wait), a recipient of the second cochlear implant system may start hearing natural sounds without any calibration delay. If time differential 1112 represents five seconds, for example, the recipient may begin hearing his or her environment or chosen sound source a full five seconds sooner than if his or her cochlear implant system lacked the implementation of system 100 that the second cochlear implant system incorporates. Moreover, the benefits runtime adaptive RF power control may be even more pronounced in the case in which session 1100-1 represents a conventional cochlear implant system (i.e., a system that performs the dedicated calibration procedure once and then relies on the generated model thereafter without the ability to perform runtime adaptive RF power control according to methods and systems described herein). This is because, in such conventional systems, calibration mode 1104-1 may actually be required again when operating mode 1106-1 with Program A switches to operating mode 1106-2 with Program B (e.g., if a different target metric is associated with the Program B, etc.). This additional stretch of time in the calibration mode is not shown in FIG. 11 because it may not be included for the mixed implementation case (i.e., for system in which runtime adaptive RF power control is implemented and the dedicated calibration procedure is merely used to generate an initial calibrated power level mapping function at startup). It will be understood, however, that avoiding the calibration mode between different sound processing programs (e.g., when switching from operating mode 1106-1 to operating mode 1106-2) may be highly advantageous since the recipient's hearing will not need to be interrupted when making the switch.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory (DRAM), which typically constitutes a main memory. Common forms of computer-readable media include, for example, a disk, hard disk, magnetic tape, any other magnetic medium, a compact disc read-only memory (CD-ROM), a digital video disc (DVD), any other optical medium, random access memory (RAM), programmable read-only memory (PROM), electrically erasable programmable read-only memory (EPROM), FLASH-EEPROM, any other memory chip or cartridge, or any other tangible medium from which a computer can read.

Figure 12:
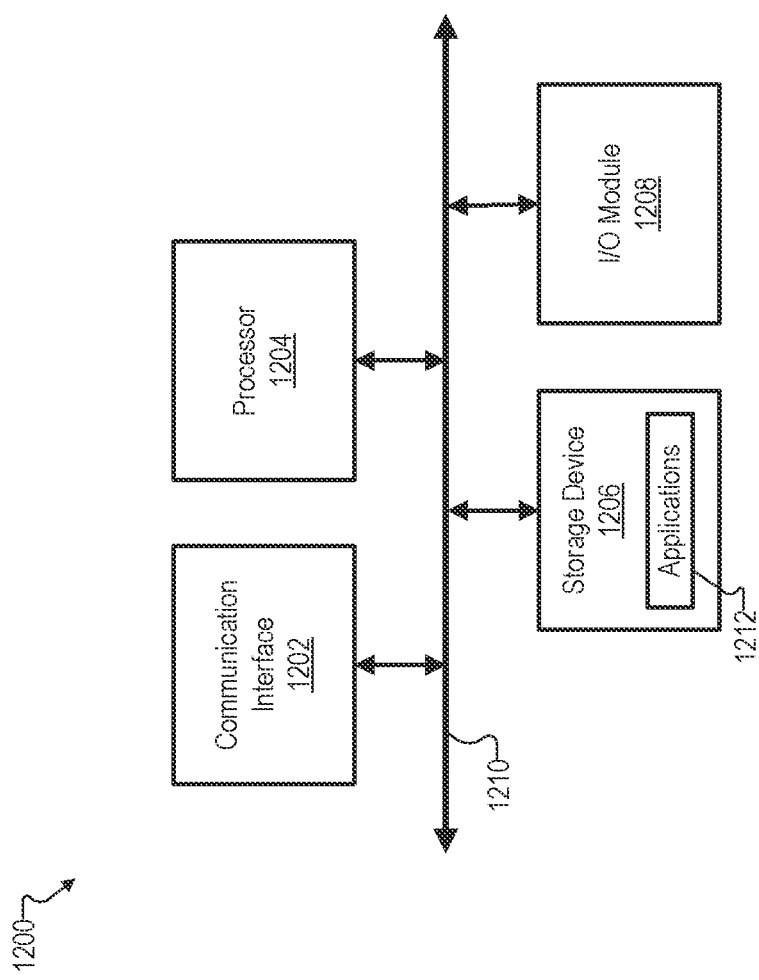
FIG. 12 shows an illustrative computing system that may implement RF power control systems and/or other computing systems and devices described herein.

FIG. 12 shows an illustrative computing system 1200 that may implement RF power control systems and/or other computing systems and devices described herein. For example, computing system 1200 may include or implement (or partially implement) an RF power control system such as system 100 or system 200, or any component included therein or system associated therewith. In some examples, computing system 1200 may be implemented or included within a cochlear implant system component (e.g., a sound processor, a headpiece, a cochlear implant, etc.) or a system associated with a cochlear implant system (e.g., computing device 412).

As shown in FIG. 12, computing system 1200 may include a communication interface 1202, a processor 1204, a storage device 1206, and an input/output (I/O) module 1208 communicatively connected via a communication infrastructure 1210. While an illustrative computing system 1200 is shown in FIG. 12, the components illustrated in FIG. 12 are not intended to be limiting. Additional or alternative components may be used in other embodiments. Components of computing system 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1206. For example, data representative of one or more executable applications 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing system 1200. For example, one or more applications 1212 residing within storage device 1206 may be configured to direct processor 1204 to perform one or more processes or functions associated with processor 104 of system 100. Likewise, memory 102 of system 100 may be implemented by or within storage device 1206.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a radio frequency (RF) transmitter configured to operate external to a recipient;
a cochlear implant configured to operate internal to the recipient based on RF power received from the RF transmitter; and
a processor communicatively coupled to the RF transmitter and the implant and configured to execute a set of instructions to:
operate in a power adaptation mode during which the processor directs the cochlear implant to apply, to the recipient, electrical stimulation configured to convey a sense of hearing to the recipient; and
while operating in the power adaptation mode:
receive an audio signal representative of audio content to be conveyed to the recipient;
direct the RF transmitter to provide the RF power to the cochlear implant at a power level determined based on the audio signal and based on a power level mapping function;
determine an error value representing a difference between a target metric and a measured metric associated with receipt of the RF power at the cochlear implant; and
update the power level mapping function based on the error value.

2. The system of claim 1, wherein the audio content includes environmental sound captured, while the processor operates in the power adaptation mode, by a microphone worn by the recipient.

3. The system of claim 1, wherein the audio signal is provided to the processor by an audio source communicatively coupled to the processor.

4. The system of claim 1, wherein:
the processor is configured to operate external to the recipient and to direct the cochlear implant by way of forward telemetry communication;
the cochlear implant is configured to detect the measured metric and transmit the error value or the measured metric to the processor by way of backward telemetry communication; and
the determining of the error value comprises at least one of:
receiving the error value from the cochlear implant by way of the backward telemetry communication, or
receiving the measured metric from the cochlear implant by way of the backward telemetry communication and calculating the error value based on the measured metric.

5. The system of claim 1, wherein the directing of the RF transmitter to provide the RF power to the cochlear implant at the power level comprises determining the power level based on the audio signal and based on the power level mapping function by:
computing an average stimulation current used by the cochlear implant to apply the electrical stimulation for the audio signal; and
designating the power level to be an output of the power level mapping function when the average stimulation current is input into the power level mapping function.

6. The system of claim 1, wherein the directing of the RF transmitter to provide the RF power to the cochlear implant at the power level comprises determining the power level based on the audio signal and based on the power level mapping function by:
sensing a power load imposed by the cochlear implant; and
designating the power level to be an output of the power level mapping function when the sensed power load is input into the power level mapping function.

7. The system of claim 1, wherein the directing of the RF transmitter to provide the RF power to the cochlear implant at the power level comprises determining the power level based on the audio signal and based on the power level mapping function by:
detecting a characteristic of the audio signal; and
designating the power level to be an output of the power level mapping function when the detected characteristic of the audio signal is input into the power level mapping function.

8. The system of claim 1, wherein the power level mapping function is a linear function defined by a slope parameter and an offset parameter.

9. The system of claim 1, wherein the power level mapping function is a piecewise-defined function including:
a plurality of continuous or discontinuous linear sub-functions; or
a plurality of continuous or discontinuous non-linear sub-functions.

10. The system of claim 1, wherein the updating of the power level mapping function based on the error value is performed using at least one of:
a Kalman filter;
a least mean squares algorithm;
a recursive least squares algorithm;
a proportional-integral-derivative control loop; or
an artificial intelligence technology.

11. The system of claim 1, wherein the processor is further configured to execute the instructions to initialize the power level mapping function, prior to the updating of the power level mapping function, based on a predetermined function configured to cause the power level at which the RF power is provided to be at least a maximum power level used by the cochlear implant to apply the electrical stimulation.

12. The system of claim 1, wherein the processor is further configured to execute the instructions to:
operate, prior to operating in the power adaptation mode, in a calibration mode during which the processor performs a dedicated calibration procedure to determine an initial calibrated power level mapping function; and
initialize the power level mapping function, prior to the updating of the power level mapping function, based on the initial calibrated power level mapping function determined as part of the dedicated calibration procedure in the calibration mode.

13. The system of claim 1, wherein the processor is further configured to execute the instructions to initialize the power level mapping function, prior to the updating of the power level mapping function, based on a previously-used function used and stored by the system during a previous operating session in the power adaptation mode.

14. The system of claim 1, wherein:
the updating of the power level mapping function is performed at an update rate; and
the processor is further configured to execute the instructions to determine the update rate based on one or more of:
a detected variance in electrical stimulation applied by the cochlear implant,
a detected error in a feedback signal representative of the measured metric,
a detected fluctuation, of an input into the power level mapping function, between different sub-functions of the power level mapping function, or
a transit effect of the RF power.

15. A system comprising:
a memory storing instructions; and
a processor communicatively coupled to the memory and configured to execute the instructions to:
operate in a power adaptation mode during which the processor directs a cochlear implant implanted within a recipient to apply, to the recipient, electrical stimulation configured to convey a sense of hearing to the recipient; and
while operating in the power adaptation mode:
receive an audio signal representative of audio content to be conveyed to the recipient;
direct a radio frequency (RF) transmitter operating external to the recipient to provide RF power to the cochlear implant at a power level determined based on the audio signal and based on a power level mapping function;
determine an error value representing a difference between a target metric and a measured metric associated with receipt of the RF power at the cochlear implant; and
update the power level mapping function based on the error value.

16. A method comprising:
operating, by a cochlear implant system that includes a radio frequency (RF) transmitter operating external to a recipient and a cochlear implant operating internal to the recipient, in a power adaptation mode during which the cochlear implant system directs the cochlear implant to apply, to the recipient, electrical stimulation configured to convey a sense of hearing to the recipient; and
while the cochlear implant system operates in the power adaptation mode:
receiving an audio signal representative of audio content to be conveyed to the recipient;
directing the RF transmitter to provide RF power to the cochlear implant at a power level determined based on the audio signal and based on a power level mapping function;
determining an error value representing a difference between a target metric and a measured metric associated with receipt of the RF power at the cochlear implant; and
updating the power level mapping function based on the error value.

17. The method of claim 16, wherein:
the electrical stimulation is representative of the audio signal; and
the audio content includes environmental sound captured, while the cochlear implant system operates in the power adaptation mode, by a microphone worn by the recipient.

18. The method of claim 16, wherein:
a processor of the cochlear implant system is configured to operate external to the recipient and to perform the directing of the cochlear implant by way of forward telemetry communication;
the cochlear implant is configured to detect the measured metric and transmit the error value or the measured metric to the processor by way of backward telemetry communication; and
the determining of the error value is performed by the processor and comprises at least one of:
receiving the error value from the cochlear implant by way of the backward telemetry communication, or
receiving the measured metric from the cochlear implant by way of the backward telemetry communication and calculating the error value based on the measured metric.

19. The method of claim 16, wherein the directing of the RF transmitter to provide the RF power to the cochlear implant at the power level comprises determining the power level based on the audio signal and based on the power level mapping function by:
computing an average stimulation current used by the cochlear implant to apply the electrical stimulation for the audio signal; and
designating the power level to be an output of the power level mapping function when the average stimulation current is input into the power level mapping function.

20. The method of claim 16, wherein:
the updating of the power level mapping function is performed at an update rate; and
the method further comprises determining, by the cochlear implant system and while the cochlear implant system operates in the power adaptation mode, the update rate based on one or more of:
a detected variance in electrical stimulation applied by the cochlear implant,
a detected error in a feedback signal representative of the measured metric,
a detected fluctuation, of an input into the power level mapping function, between different sub-functions of the power level mapping function, or
a transit effect of the RF power.

* * * * *